United States Patent
McGuckin, Jr. et al.

(10) Patent No.: US 8,414,543 B2
(45) Date of Patent: Apr. 9, 2013

(54) ROTATIONAL THROMBECTOMY WIRE WITH BLOCKING DEVICE

(75) Inventors: James F. McGuckin, Jr., Radnor, PA (US); John D. Leedle, Philadelphia, PA (US); James Erich Bressler, Langhorne, PA (US); Peter W. J. Hinchliffe, Campbell Hall, NY (US)

(73) Assignee: Rex Medical, L.P., Conshohocken, PA (US)

( * ) Notice: Subject to any disclaimer, the term of this patent is extended or adjusted under 35 U.S.C. 154(b) by 241 days.

(21) Appl. No.: 12/861,110

(22) Filed: Aug. 23, 2010

(65) Prior Publication Data
US 2011/0040314 A1  Feb. 17, 2011

Related U.S. Application Data

(63) Continuation of application No. 12/631,787, filed on Dec. 4, 2009, now Pat. No. 7,909,801, which is a continuation of application No. 11/267,379, filed on Nov. 4, 2005, now Pat. No. 7,645,261, which is a continuation of application No. 09/888,149, filed on Jun. 22, 2001, now abandoned, which is a continuation-in-part of application No. PCT/US00/41355, filed on Oct. 20, 2000.

(60) Provisional application No. 60/214,331, filed on Jun. 27, 2000, provisional application No. 60/161,124, filed on Oct. 22, 1999.

(51) Int. Cl.
*A61M 5/00*  (2006.01)
(52) U.S. Cl.
USPC ....................................... 604/247

(58) Field of Classification Search ............... 604/96.01, 604/101.01, 97.01–97.03, 99.01–99.04, 101.02–101.05, 604/102.01–102.03, 103.07, 104, 915, 916, 604/22, 27, 35, 266, 267
See application file for complete search history.

(56) References Cited

U.S. PATENT DOCUMENTS

| | | | |
|---|---|---|---|
| 2,556,783 A | 6/1951 | Wallace | |
| 2,756,752 A | 7/1956 | Scherlis | |

(Continued)

FOREIGN PATENT DOCUMENTS

| | | |
|---|---|---|
| DE | 1075903 | 2/1960 |
| DE | 3640034 | 5/1988 |

(Continued)

OTHER PUBLICATIONS

Rex Medical website—www.rexmedical.com—home page (Jul. 2000).

(Continued)

*Primary Examiner* — Manuel Mendez
(74) *Attorney, Agent, or Firm* — Neil D. Gershon

(57) ABSTRACT

A thrombectomy apparatus for breaking up thrombus or other obstructive material in a lumen of a vascular graft or vessel. The apparatus includes a wire having a first configuration and a second deployed configuration, the wire having a straighter configuration in the first configuration. The wire is operatively connected to a motor for rotation of the wire to contact and break up the thrombus or other obstructive material. A blocking device at a distal portion of the apparatus is movable between a collapsed configuration and an expanded configuration, and is configured in the expanded configuration to block thrombus dislodged by rotation of the wire.

22 Claims, 13 Drawing Sheets

U.S. PATENT DOCUMENTS

| | | |
|---|---|---|
| 3,108,594 A | 10/1963 | Glassman |
| 3,612,058 A | 10/1971 | Ackerman |
| 3,741,214 A | 6/1973 | Tillander |
| 3,749,085 A | 7/1973 | Willson et al. |
| 3,841,308 A | 10/1974 | Tate |
| 4,030,503 A | 6/1977 | Clark, III |
| 4,276,874 A | 7/1981 | Wolvek et al. |
| 4,425,908 A | 1/1984 | Simon |
| 4,559,046 A | 12/1985 | Groshong et al. |
| 4,579,127 A | 4/1986 | Haacke |
| 4,614,188 A | 9/1986 | Bazell et al. |
| 4,646,736 A | 3/1987 | Auth |
| 4,664,112 A | 5/1987 | Kensey et al. |
| 4,676,778 A | 6/1987 | Nelson, Jr. |
| 4,706,671 A | 11/1987 | Weinrib |
| 4,732,154 A | 3/1988 | Shiber |
| 4,745,919 A | 5/1988 | Bundy et al. |
| 4,790,812 A * | 12/1988 | Hawkins et al. ............... 604/22 |
| 4,794,928 A | 1/1989 | Kletschka |
| 4,819,634 A | 4/1989 | Shiber |
| 4,873,978 A | 10/1989 | Ginsburg |
| 4,883,460 A | 11/1989 | Zanetti |
| 4,906,244 A | 3/1990 | Pinchuk et al. |
| 4,935,025 A | 6/1990 | Bundy et al. |
| 4,984,581 A | 1/1991 | Stice |
| 4,986,807 A | 1/1991 | Farr |
| 4,990,134 A | 2/1991 | Auth |
| 4,994,067 A | 2/1991 | Summers |
| 5,002,553 A | 3/1991 | Shiber |
| RE33,569 E | 4/1991 | Gifford et al. |
| 5,007,896 A | 4/1991 | Shiber |
| 5,009,659 A | 4/1991 | Hamlin et al. |
| 5,011,488 A | 4/1991 | Ginsburg |
| 5,011,489 A | 4/1991 | Salem |
| 5,011,490 A | 4/1991 | Fischell et al. |
| 5,019,088 A | 5/1991 | Farr |
| 5,019,089 A | 5/1991 | Farr |
| 5,024,651 A | 6/1991 | Shiber |
| 5,026,383 A | 6/1991 | Nobles |
| 5,026,384 A | 6/1991 | Farr et al. |
| 5,041,217 A | 8/1991 | Reid |
| 5,042,984 A | 8/1991 | Kensey et al. |
| 5,047,040 A | 9/1991 | Simpson et al. |
| 5,047,041 A | 9/1991 | Samuels |
| 5,049,124 A | 9/1991 | Bales |
| 5,049,154 A | 9/1991 | Quadri |
| 5,053,044 A | 10/1991 | Mueller et al. |
| 5,054,501 A | 10/1991 | Chuttani et al. |
| 5,059,203 A | 10/1991 | Husted |
| 5,061,240 A | 10/1991 | Cherian |
| 5,062,648 A | 11/1991 | Gomringer |
| 5,069,662 A | 12/1991 | Bodden |
| 5,069,679 A | 12/1991 | Taheri |
| 5,071,424 A | 12/1991 | Reger |
| 5,071,425 A | 12/1991 | Gifford et al. |
| 5,074,841 A | 12/1991 | Ademovic et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,264 A | 2/1992 | Miller et al. |
| 5,087,265 A | 2/1992 | Summers |
| 5,092,839 A | 3/1992 | Kipperman |
| 5,092,872 A | 3/1992 | Segalowitz |
| 5,092,873 A | 3/1992 | Simpson et al. |
| 5,097,849 A | 3/1992 | Kensey et al. |
| 5,100,423 A | 3/1992 | Fearnot |
| 5,100,424 A | 3/1992 | Jang et al. |
| 5,100,425 A | 3/1992 | Fischell et al. |
| 5,100,426 A | 3/1992 | Nixon |
| 5,102,415 A | 4/1992 | Guenther |
| 5,108,411 A | 4/1992 | McKenzie |
| 5,108,419 A | 4/1992 | Reger et al. |
| 5,112,347 A | 5/1992 | Taheri |
| 5,114,399 A | 5/1992 | Kovalcheck |
| 5,116,350 A | 5/1992 | Stevens |
| 5,116,352 A | 5/1992 | Schnepp-Pesch et al. |
| 5,127,902 A | 7/1992 | Fischell |
| 5,127,917 A | 7/1992 | Niederhauser et al. |
| 5,131,379 A | 7/1992 | Sewell |
| 5,133,725 A | 7/1992 | Quadri |
| 5,135,482 A | 8/1992 | Neracher |
| 5,135,484 A | 8/1992 | Wright |
| 5,135,531 A | 8/1992 | Shiber |
| 5,139,506 A | 8/1992 | Bush |
| 5,141,491 A | 8/1992 | Bowald |
| 5,141,503 A | 8/1992 | Sewell |
| 5,152,771 A | 10/1992 | Sabbaghian et al. |
| 5,152,772 A | 10/1992 | Sewell |
| 5,152,773 A | 10/1992 | Redha |
| 5,154,724 A | 10/1992 | Andrews |
| 5,156,610 A | 10/1992 | Reger |
| 5,158,564 A | 10/1992 | Schnepp-Pesch et al. |
| 5,160,342 A | 11/1992 | Reger et al. |
| 5,163,421 A | 11/1992 | Bernstein et al. |
| 5,170,805 A | 12/1992 | Kensey et al. |
| 5,171,316 A | 12/1992 | Mehigan |
| 5,176,693 A | 1/1993 | Pannek |
| 5,178,625 A | 1/1993 | Groshong |
| 5,181,920 A | 1/1993 | Mueller et al. |
| 5,192,268 A | 3/1993 | Shiber |
| 5,192,286 A | 3/1993 | Phan et al. |
| 5,192,290 A | 3/1993 | Hilal |
| 5,192,291 A | 3/1993 | Pannek |
| 5,195,954 A | 3/1993 | Schnepp-Pesch et al. |
| 5,195,956 A | 3/1993 | Stockmeier |
| 5,196,024 A | 3/1993 | Barath |
| 5,197,485 A | 3/1993 | Grooters |
| 5,201,750 A | 4/1993 | Hecherl et al. |
| 5,203,772 A | 4/1993 | Hammerslag et al. |
| 5,209,749 A | 5/1993 | Buelna |
| 5,211,651 A | 5/1993 | Reger et al. |
| 5,211,683 A | 5/1993 | Maginot |
| 5,217,026 A | 6/1993 | Stoy et al. |
| 5,217,453 A | 6/1993 | Wilk |
| 5,217,474 A | 6/1993 | Zacca et al. |
| 5,222,965 A | 6/1993 | Haughton |
| 5,222,966 A | 6/1993 | Perkins et al. |
| 5,224,945 A | 7/1993 | Pannek |
| 5,224,949 A | 7/1993 | Gomringer et al. |
| 5,226,909 A | 7/1993 | Evans et al. |
| 5,234,450 A | 8/1993 | Segalowitz |
| 5,234,451 A | 8/1993 | Osypka |
| 5,242,460 A | 9/1993 | Klein et al. |
| 5,242,461 A | 9/1993 | Kortenback et al. |
| 5,248,296 A | 9/1993 | Alliger |
| 5,250,059 A | 10/1993 | Andreas et al. |
| 5,250,060 A | 10/1993 | Carbo et al. |
| 5,251,640 A | 10/1993 | Osborne |
| 5,261,877 A | 11/1993 | Fine et al. |
| 5,262,593 A | 11/1993 | Madry et al. |
| 5,267,954 A | 12/1993 | Nita |
| 5,269,751 A | 12/1993 | Kaliman et al. |
| 5,269,793 A | 12/1993 | Simpson |
| 5,282,484 A | 2/1994 | Reger |
| 5,282,813 A | 2/1994 | Redha |
| 5,284,478 A | 2/1994 | Nobles et al. |
| 5,284,486 A | 2/1994 | Kotula et al. |
| 5,295,958 A | 3/1994 | Shturman |
| 5,300,025 A | 4/1994 | Wantink |
| 5,303,719 A | 4/1994 | Wilk et al. |
| 5,304,189 A | 4/1994 | Goldberg et al. |
| 5,304,220 A | 4/1994 | Maginot |
| 5,306,244 A | 4/1994 | Shiber |
| 5,308,354 A | 5/1994 | Zacca et al. |
| 5,312,425 A | 5/1994 | Evans et al. |
| 5,312,427 A | 5/1994 | Shturman |
| 5,313,967 A | 5/1994 | Lieber et al. |
| 5,314,407 A | 5/1994 | Auth et al. |
| 5,314,438 A | 5/1994 | Shturman |
| 5,318,576 A | 6/1994 | Plassche et al. |
| 5,320,599 A | 6/1994 | Griep et al. |
| 5,320,634 A | 6/1994 | Vigil et al. |
| 5,334,211 A | 8/1994 | Shiber |
| 5,336,167 A | 8/1994 | Sullivan et al. |
| 5,336,234 A | 8/1994 | Vigil et al. |
| 5,342,394 A | 8/1994 | Matsuno et al. |

| | | |
|---|---|---|
| 5,344,395 A | 9/1994 | Whalen et al. |
| 5,345,940 A | 9/1994 | Seward et al. |
| 5,345,945 A | 9/1994 | Hodgson et al. |
| 5,346,473 A | 9/1994 | Bowman |
| 5,348,017 A | 9/1994 | Thornton et al. |
| 5,350,390 A | 9/1994 | Sher |
| 5,352,232 A | 10/1994 | Cohen |
| 5,356,418 A | 10/1994 | Shturman |
| 5,358,472 A | 10/1994 | Vance et al. |
| 5,358,485 A | 10/1994 | Vance et al. |
| 5,358,507 A | 10/1994 | Daily |
| 5,358,509 A | 10/1994 | Fine et al. |
| 5,360,432 A | 11/1994 | Shturman |
| 5,360,433 A | 11/1994 | Medl |
| 5,366,463 A | 11/1994 | Ryan |
| 5,366,464 A | 11/1994 | Belknap |
| 5,368,603 A | 11/1994 | Halliburton |
| 5,370,609 A | 12/1994 | Drasler et al. |
| 5,370,651 A | 12/1994 | Summers |
| 5,370,653 A | 12/1994 | Cragg |
| 5,372,144 A | 12/1994 | Mortier et al. |
| 5,372,601 A | 12/1994 | Lary |
| 5,376,100 A | 12/1994 | Lefebvre et al. |
| 5,383,460 A | 1/1995 | Jang et al. |
| 5,395,311 A | 3/1995 | Andrews |
| 5,395,315 A | 3/1995 | Griep |
| 5,395,384 A | 3/1995 | Duthoit |
| 5,402,790 A | 4/1995 | Jang et al. |
| 5,403,334 A | 4/1995 | Evans et al. |
| 5,409,454 A | 4/1995 | Fischell et al. |
| 5,411,509 A | 5/1995 | Hilal |
| 5,417,703 A | 5/1995 | Brown et al. |
| 5,419,774 A | 5/1995 | Willard et al. |
| 5,421,832 A | 6/1995 | Lefebvre |
| 5,423,799 A | 6/1995 | Shiu |
| 5,423,838 A | 6/1995 | Willard |
| 5,429,136 A | 7/1995 | Milo et al. |
| 5,441,510 A | 8/1995 | Simpson et al. |
| 5,449,369 A | 9/1995 | Imran |
| 5,449,372 A | 9/1995 | Schmaltz et al. |
| 5,451,208 A | 9/1995 | Goldrath |
| 5,453,088 A | 9/1995 | Boudewijn et al. |
| 5,462,529 A | 10/1995 | Simpson et al. |
| 5,476,450 A | 12/1995 | Ruggio |
| 5,480,370 A | 1/1996 | Gelsinger |
| 5,484,412 A | 1/1996 | Pierpont |
| 5,488,958 A | 2/1996 | Topel et al. |
| 5,490,859 A | 2/1996 | Mische et al. |
| 5,496,267 A | 3/1996 | Drasler et al. |
| 5,497,782 A | 3/1996 | Fugoso |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,092 A | 5/1996 | Forman et al. |
| 5,514,115 A | 5/1996 | Frantzen et al. |
| 5,514,150 A | 5/1996 | Rostoker |
| 5,514,151 A | 5/1996 | Fogarty et al. |
| 5,520,635 A | 5/1996 | Gelbfish |
| 5,522,824 A | 6/1996 | Ashby |
| 5,522,825 A | 6/1996 | Kropf et al. |
| 5,522,826 A | 6/1996 | Daily |
| 5,527,325 A | 6/1996 | Conley et al. |
| 5,527,326 A | 6/1996 | Hermann et al. |
| 5,527,327 A | 6/1996 | Louw et al. |
| 5,527,330 A | 6/1996 | Tovey |
| 5,536,242 A | 7/1996 | Willard et al. |
| 5,540,656 A | 7/1996 | Pflueger et al. |
| 5,540,707 A | 7/1996 | Ressemann et al. |
| 5,542,917 A | 8/1996 | Nita et al. |
| 5,542,925 A | 8/1996 | Orth |
| 5,547,469 A | 8/1996 | Rowland et al. |
| 5,551,443 A | 9/1996 | Sepetka et al. |
| 5,554,163 A | 9/1996 | Shturman |
| 5,556,405 A | 9/1996 | Lary |
| 5,556,408 A | 9/1996 | Farhat |
| 5,562,275 A | 10/1996 | Weissenfluh et al. |
| 5,562,701 A | 10/1996 | Huiteme et al. |
| 5,569,179 A | 10/1996 | Adrian et al. |
| 5,569,204 A | 10/1996 | Cramer |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,571,122 A | 11/1996 | Kelly et al. |
| 5,571,130 A | 11/1996 | Simpson et al. |
| 5,571,167 A | 11/1996 | Maginot |
| 5,584,842 A | 12/1996 | Fogarty et al. |
| 5,584,843 A | 12/1996 | Wulfman et al. |
| 5,591,183 A | 1/1997 | Chin |
| 5,591,184 A | 1/1997 | McDonnell et al. |
| 5,599,307 A | 2/1997 | Bacher et al. |
| 5,601,580 A | 2/1997 | Goldberg et al. |
| 5,601,581 A | 2/1997 | Fogarty et al. |
| 5,605,162 A | 2/1997 | Mirzaee et al. |
| 5,609,602 A | 3/1997 | Machemer et al. |
| 5,616,149 A | 4/1997 | Barath |
| 5,622,188 A | 4/1997 | Plaia et al. |
| 5,624,455 A | 4/1997 | Matsuno |
| 5,624,457 A | 4/1997 | Farley et al. |
| 5,626,562 A | 5/1997 | Castro |
| 5,626,593 A | 5/1997 | Imran |
| 5,626,597 A | 5/1997 | Urban et al. |
| 5,626,602 A | 5/1997 | Gianotti et al. |
| 5,628,746 A | 5/1997 | Clayman |
| 5,628,761 A | 5/1997 | Rizik |
| 5,630,823 A | 5/1997 | Schmitz-Rode et al. |
| 5,632,755 A | 5/1997 | Nordgren et al. |
| 5,643,199 A | 7/1997 | Rowland et al. |
| 5,643,296 A | 7/1997 | Hundertmark et al. |
| 5,643,297 A | 7/1997 | Nordgren et al. |
| 5,643,298 A | 7/1997 | Nordgren et al. |
| 5,649,941 A | 7/1997 | Lary |
| 5,649,946 A | 7/1997 | Bramlet |
| 5,653,722 A | 8/1997 | Kieturakis |
| 5,658,282 A | 8/1997 | Daw et al. |
| 5,658,296 A | 8/1997 | Bates et al. |
| 5,658,301 A | 8/1997 | Lemaitre et al. |
| 5,658,302 A | 8/1997 | Wicherski et al. |
| 5,662,603 A | 9/1997 | Gelbfish |
| 5,662,671 A | 9/1997 | Barbut et al. |
| 5,662,701 A | 9/1997 | Plaia et al. |
| 5,665,093 A | 9/1997 | Atkins |
| 5,665,098 A | 9/1997 | Kelly et al. |
| 5,667,480 A | 9/1997 | Knight et al. |
| 5,669,920 A | 9/1997 | Conley |
| 5,674,226 A | 10/1997 | Doherty et al. |
| 5,674,232 A | 10/1997 | Halliburton |
| 5,681,335 A | 10/1997 | Serra et al. |
| 5,681,336 A | 10/1997 | Clement et al. |
| 5,683,362 A | 11/1997 | Rowland et al. |
| 5,688,234 A | 11/1997 | Frisbie |
| 5,695,506 A | 12/1997 | Pike et al. |
| 5,695,507 A | 12/1997 | Auth et al. |
| 5,695,508 A | 12/1997 | Chigogidze |
| 5,695,514 A | 12/1997 | Chin |
| 5,697,944 A | 12/1997 | Lary |
| 5,700,240 A | 12/1997 | Barwick et al. |
| 5,702,412 A | 12/1997 | Popov et al. |
| 5,702,413 A | 12/1997 | Lafontaine |
| 5,720,764 A | 2/1998 | Naderlinger |
| 5,725,552 A | 3/1998 | Kotula et al. |
| 5,728,123 A | 3/1998 | Lemelson et al. |
| 5,733,296 A | 3/1998 | Rogers et al. |
| 5,746,758 A | 5/1998 | Nordgren et al. |
| 5,755,968 A | 5/1998 | Stone |
| 5,762,637 A | 6/1998 | Berg et al. |
| 5,766,191 A | 6/1998 | Trerotola |
| 5,766,192 A | 6/1998 | Zacca |
| 5,776,153 A | 7/1998 | Rees |
| 5,814,064 A | 9/1998 | Daniel et al. |
| 5,827,324 A | 10/1998 | Cassell et al. |
| 5,830,156 A | 11/1998 | Ali |
| 5,833,631 A | 11/1998 | Nguyen |
| 5,833,644 A | 11/1998 | Zadno-Azizi et al. |
| 5,840,046 A | 11/1998 | Deem |
| 5,843,103 A | 12/1998 | Wulfman |

| | | | |
|---|---|---|---|
| 5,848,964 A | 12/1998 | Samuels | |
| 5,876,413 A | 3/1999 | Fogarty et al. | |
| 5,876,414 A | 3/1999 | Straub | |
| 5,882,329 A | 3/1999 | Patterson et al. | |
| 5,885,227 A | 3/1999 | Finlayson | |
| 5,895,398 A | 4/1999 | Wensel et al. | |
| 5,902,263 A | 5/1999 | Patterson et al. | |
| 5,902,268 A | 5/1999 | Saab | |
| 5,904,679 A | 5/1999 | Clayman | |
| 5,910,364 A | 6/1999 | Miyata et al. | |
| 5,916,166 A | 6/1999 | Reiss et al. | |
| 5,919,163 A | 7/1999 | Glickman | |
| 5,938,623 A | 8/1999 | Quiachon et al. | |
| 5,941,869 A * | 8/1999 | Patterson et al. | 604/508 |
| 5,941,896 A | 8/1999 | Kerr | |
| 5,947,985 A | 9/1999 | Imran | |
| 5,954,737 A | 9/1999 | Lee | |
| 5,971,991 A | 10/1999 | Sunderland | |
| 5,972,019 A | 10/1999 | Engelson et al. | |
| 5,984,877 A | 11/1999 | Fleischhacker, Jr. | |
| 5,984,947 A | 11/1999 | Smith | |
| 6,001,068 A | 12/1999 | Uchino et al. | |
| 6,001,112 A | 12/1999 | Taylor | |
| 6,001,118 A | 12/1999 | Daniel et al. | |
| 6,004,279 A | 12/1999 | Crowley et al. | |
| 6,019,736 A | 2/2000 | Avellanet et al. | |
| 6,022,336 A | 2/2000 | Zadno-Azizi et al. | |
| 6,022,363 A | 2/2000 | Walker et al. | |
| 6,027,520 A | 2/2000 | Tsugita et al. | |
| 6,030,397 A | 2/2000 | Monetti et al. | |
| 6,036,708 A | 3/2000 | Sciver | |
| 6,056,721 A | 5/2000 | Shulze | |
| 6,056,770 A | 5/2000 | Epstein et al. | |
| 6,066,149 A | 5/2000 | Samson et al. | |
| 6,066,158 A | 5/2000 | Engelson et al. | |
| 6,080,170 A | 6/2000 | Nash et al. | |
| 6,080,178 A | 6/2000 | Meglin | |
| RE36,764 E | 7/2000 | Zacca et al. | |
| 6,083,198 A | 7/2000 | Afzal | |
| 6,090,118 A | 7/2000 | McGuckin, Jr. | |
| 6,096,053 A | 8/2000 | Bates | |
| 6,102,884 A | 8/2000 | Squitieri | |
| 6,113,614 A | 9/2000 | Mears | |
| 6,123,715 A | 9/2000 | Amplatz | |
| 6,126,635 A | 10/2000 | Simpson et al. | |
| 6,129,739 A | 10/2000 | Khosravi | |
| 6,129,750 A | 10/2000 | Tockman et al. | |
| 6,143,009 A | 11/2000 | Shiber | |
| 6,146,396 A | 11/2000 | Konya et al. | |
| 6,146,397 A | 11/2000 | Harkrider, Jr. | |
| 6,152,909 A | 11/2000 | Bagaoisan et al. | |
| 6,152,946 A | 11/2000 | Broome et al. | |
| 6,156,046 A | 12/2000 | Passafaro et al. | |
| 6,165,567 A | 12/2000 | Ventzek et al. | |
| 6,168,570 B1 | 1/2001 | Ferrera | |
| 6,168,579 B1 | 1/2001 | Tsugita | |
| 6,171,327 B1 | 1/2001 | Daniel et al. | |
| 6,179,851 B1 | 1/2001 | Barbut et al. | |
| 6,179,861 B1 | 1/2001 | Khosravi et al. | |
| 6,183,487 B1 | 2/2001 | Barry et al. | |
| 6,185,449 B1 | 2/2001 | Berg et al. | |
| 6,187,025 B1 | 2/2001 | Machek | |
| 6,193,735 B1 | 2/2001 | Stevens | |
| 6,203,561 B1 | 3/2001 | Ramee et al. | |
| 6,206,898 B1 | 3/2001 | Honeycutt et al. | |
| 6,217,595 B1 | 4/2001 | Shturman et al. | |
| 6,221,042 B1 | 4/2001 | Adams | |
| 6,224,620 B1 | 5/2001 | Maahs | |
| 6,231,588 B1 | 5/2001 | Zadno-Azizi | |
| 6,235,043 B1 | 5/2001 | Reiley et al. | |
| 6,238,405 B1 | 5/2001 | Findlay, III et al. | |
| 6,245,088 B1 | 6/2001 | Lowery | |
| 6,251,086 B1 | 6/2001 | Cornelius et al. | |
| 6,254,550 B1 | 7/2001 | McNamara et al. | |
| 6,258,115 B1 | 7/2001 | Dubrul | |
| 6,264,667 B1 | 7/2001 | McGuckin, Jr. | |
| 6,264,672 B1 | 7/2001 | Fisher | |
| 6,270,509 B1 | 8/2001 | Barry et al. | |
| 6,277,139 B1 | 8/2001 | Levinson et al. | |
| 6,287,271 B1 | 9/2001 | Dubrul et al. | |
| 6,290,710 B1 | 9/2001 | Cryer et al. | |
| 6,299,623 B1 | 10/2001 | Wulfman | |
| 6,322,572 B1 | 11/2001 | Lee | |
| 6,336,934 B1 | 1/2002 | Gilson et al. | |
| 6,338,735 B1 | 1/2002 | Stevens et al. | |
| 6,340,364 B2 | 1/2002 | Kanesaka | |
| 6,346,116 B1 | 2/2002 | Brooks et al. | |
| 6,348,056 B1 | 2/2002 | Bates et al. | |
| 6,364,895 B1 | 4/2002 | Greenhalgh | |
| 6,364,900 B1 | 4/2002 | Heuser | |
| 6,368,338 B1 | 4/2002 | Konya et al. | |
| 6,371,928 B1 | 4/2002 | McFann et al. | |
| 6,371,971 B1 | 4/2002 | Tsugita et al. | |
| 6,375,670 B1 | 4/2002 | Greenhalgh | |
| 6,391,044 B1 | 5/2002 | Yadav et al. | |
| 6,402,745 B1 | 6/2002 | Wilk | |
| 6,425,909 B1 | 7/2002 | Dieck et al. | |
| 6,454,775 B1 | 9/2002 | Demarais et al. | |
| 6,454,779 B1 | 9/2002 | Taylor | |
| 6,482,215 B1 | 11/2002 | Shiber | |
| 6,482,222 B1 | 11/2002 | Bruckheimer et al. | |
| 6,485,500 B1 | 11/2002 | Kokish et al. | |
| 6,485,501 B1 | 11/2002 | Green | |
| 6,500,191 B2 | 12/2002 | Addis | |
| 6,527,979 B2 | 3/2003 | Constanta et al. | |
| 6,530,939 B1 | 3/2003 | Hopkins et al. | |
| 6,544,279 B1 | 4/2003 | Hopkins et al. | |
| 6,551,268 B1 | 4/2003 | Kaganov et al. | |
| 6,558,405 B1 | 5/2003 | McInnes | |
| 6,562,058 B2 | 5/2003 | Sequin et al. | |
| 6,569,184 B2 | 5/2003 | Huter | |
| 6,582,448 B1 | 6/2003 | Boyle et al. | |
| 6,589,263 B1 | 7/2003 | Hopkins et al. | |
| 6,592,606 B2 | 7/2003 | Huter et al. | |
| 6,592,616 B1 | 7/2003 | Stack et al. | |
| 6,596,011 B2 | 7/2003 | Johnson et al. | |
| 6,602,264 B1 | 8/2003 | McGuckin, Jr. | |
| 6,605,102 B1 | 8/2003 | Mazzocchi et al. | |
| 6,610,077 B1 | 8/2003 | Hancock et al. | |
| 6,616,679 B1 | 9/2003 | Khosravi et al. | |
| 6,616,680 B1 | 9/2003 | Thielen | |
| 6,620,182 B1 | 9/2003 | Khosravi et al. | |
| 6,635,068 B1 | 10/2003 | Dubrul et al. | |
| 6,635,070 B2 | 10/2003 | Leeflang et al. | |
| 6,638,294 B1 | 10/2003 | Palmer | |
| 6,645,220 B1 | 11/2003 | Huter et al. | |
| 6,645,223 B2 | 11/2003 | Boyle et al. | |
| 6,652,505 B1 | 11/2003 | Tsugita | |
| 6,652,554 B1 | 11/2003 | Wholey et al. | |
| 6,652,557 B1 | 11/2003 | MacDonald | |
| 6,656,202 B2 | 12/2003 | Papp et al. | |
| 6,656,203 B2 | 12/2003 | Roth et al. | |
| 6,656,207 B2 | 12/2003 | Epstein et al. | |
| 6,660,021 B1 | 12/2003 | Palmer et al. | |
| 6,663,613 B1 | 12/2003 | Evans et al. | |
| 6,663,652 B2 | 12/2003 | Daniel et al. | |
| 6,695,813 B1 | 2/2004 | Boyle et al. | |
| 6,695,865 B2 | 2/2004 | Boyle et al. | |
| 6,706,053 B1 | 3/2004 | Boylan et al. | |
| 6,706,055 B2 | 3/2004 | Douk et al. | |
| 6,716,231 B1 | 4/2004 | Rafiee et al. | |
| 6,726,701 B2 | 4/2004 | Gilson et al. | |
| 6,726,702 B2 | 4/2004 | Khosravi | |
| 6,726,703 B2 | 4/2004 | Broome et al. | |
| 6,740,061 B1 | 5/2004 | Oslund et al. | |
| 6,743,247 B1 | 6/2004 | Levinson et al. | |
| 6,746,469 B2 | 6/2004 | Mouw | |
| 6,755,847 B2 | 6/2004 | Eskuri | |
| 6,761,727 B1 | 7/2004 | Ladd | |
| 6,761,732 B2 | 7/2004 | Burkett et al. | |
| 6,773,448 B2 | 8/2004 | Kusleika et al. | |
| 6,818,006 B2 | 11/2004 | Douk et al. | |
| 6,837,898 B2 | 1/2005 | Boyle et al. | |
| 6,840,950 B2 | 1/2005 | Stanford et al. | |
| 6,911,036 B2 | 6/2005 | Douk et al. | |
| 6,918,921 B2 | 7/2005 | Brady et al. | |
| 6,929,652 B1 | 8/2005 | Andrews et al. | |
| 6,936,059 B2 | 8/2005 | Belef | |

| | | |
|---|---|---|
| 7,037,316 B2 | 5/2006 | McGuckin et al. |
| 7,115,101 B2 | 10/2006 | Cornelius et al. |
| 7,618,434 B2 | 11/2009 | Santra et al. |
| 7,819,887 B2 | 10/2010 | McGuckin et al. |
| 8,062,317 B2 | 11/2011 | McGuckin et al. |
| 2001/0009980 A1 | 7/2001 | Richardson et al. |
| 2001/0011182 A1 | 8/2001 | Dubrul et al. |
| 2001/0031981 A1 | 10/2001 | Demarais et al. |
| 2002/0087187 A1 | 7/2002 | Mazzocchi et al. |
| 2002/0095171 A1 | 7/2002 | Belef |
| 2002/0111647 A1 | 8/2002 | Khairkhahan et al. |
| 2002/0161393 A1 | 10/2002 | Demond et al. |
| 2002/0183783 A1 | 12/2002 | Shadduck |
| 2002/0193825 A1 | 12/2002 | McGuckin et al. |
| 2002/0193827 A1 | 12/2002 | McGuckin et al. |
| 2003/0004540 A1 | 1/2003 | Linder et al. |
| 2003/0004541 A1 | 1/2003 | Linder et al. |
| 2003/0045898 A1 | 3/2003 | Harrison et al. |
| 2003/0060844 A1 | 3/2003 | Borillo et al. |
| 2003/0065355 A1 | 4/2003 | Weber |
| 2003/0100917 A1 | 5/2003 | Boyle et al. |
| 2003/0100918 A1 | 5/2003 | Duane |
| 2003/0114880 A1 | 6/2003 | Hansen et al. |
| 2003/0191483 A1 | 10/2003 | Cooke et al. |
| 2004/0049223 A1 | 3/2004 | Nishtala et al. |
| 2004/0193206 A1 | 9/2004 | Gerberding et al. |
| 2005/0101988 A1 | 5/2005 | Stanford et al. |
| 2005/0177187 A1 | 8/2005 | Gray et al. |
| 2005/0216052 A1 | 9/2005 | Mazzocchi et al. |
| 2006/0074441 A1 | 4/2006 | McGuckin, Jr. et al. |
| 2006/0106407 A1 | 5/2006 | McGuckin, Jr. et al. |
| 2008/0319462 A1 | 12/2008 | Montague et al. |
| 2009/0082800 A1 | 3/2009 | Janardhan |
| 2011/0077673 A1 | 3/2011 | Grubac et al. |
| 2011/0282370 A1 | 11/2011 | Levine et al. |

FOREIGN PATENT DOCUMENTS

| | | |
|---|---|---|
| DE | 8900494 | 3/1989 |
| EP | 0177782 | 4/1986 |
| EP | 0452631 | 10/1991 |
| EP | 0709110 | 5/1996 |
| EP | 0815894 | 1/1998 |
| JP | 56020839 | 2/1981 |
| WO | WO 9601591 | 1/1996 |
| WO | WO-98/38926 | 9/1998 |
| WO | 9923958 | 5/1999 |
| WO | WO-99/56638 | 11/1999 |
| WO | WO 0007521 | 2/2000 |
| WO | WO 0007655 | 2/2000 |
| WO | WO 00/32265 | 6/2000 |
| WO | WO 0145590 | 6/2001 |
| WO | 0154754 | 8/2001 |
| WO | WO 2009/029430 | 3/2009 |

OTHER PUBLICATIONS

Bacchus Vascular Solera Thrombectomy Catheter Brochure (Jan. 4, 2002).

\* cited by examiner

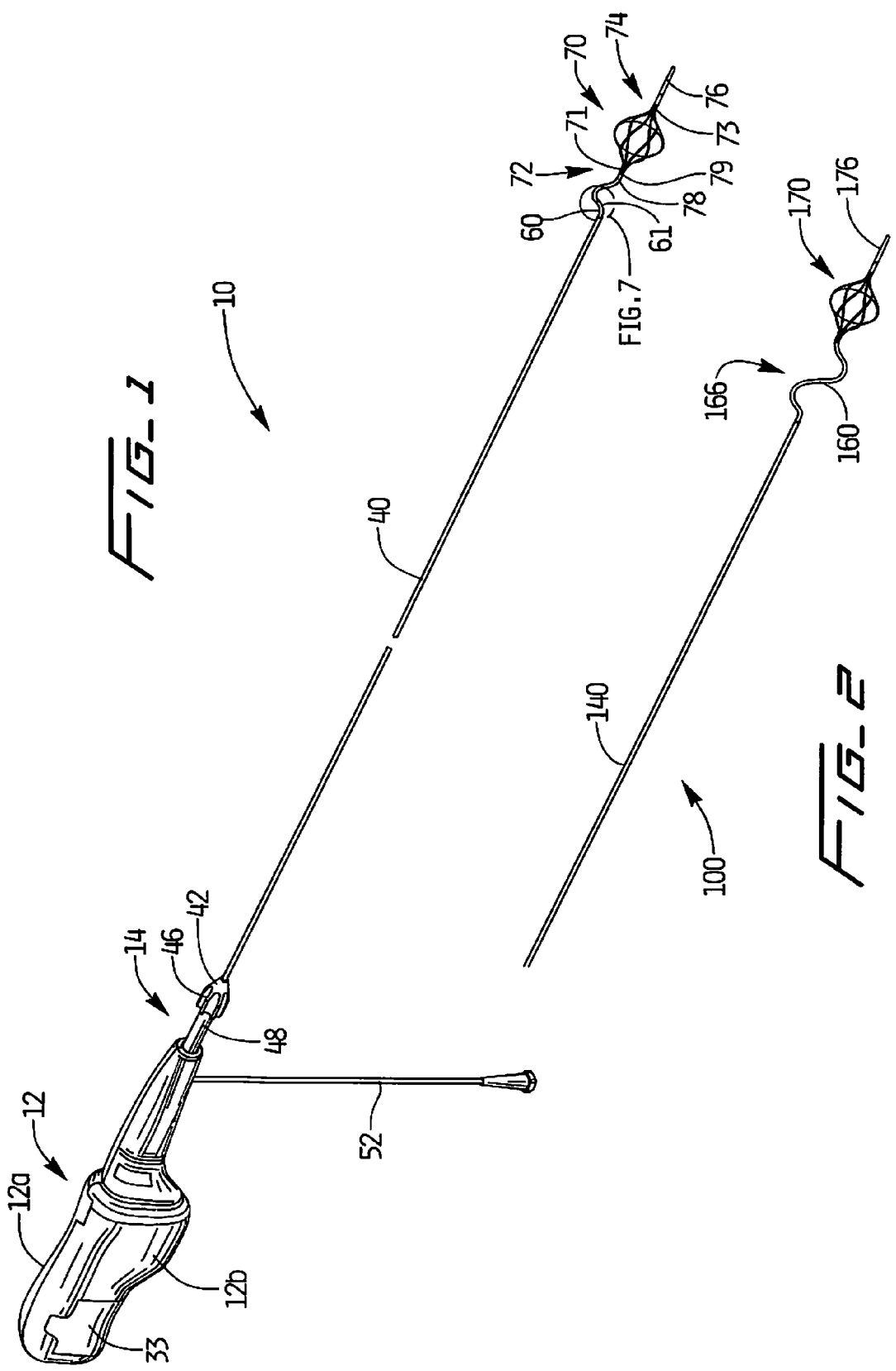

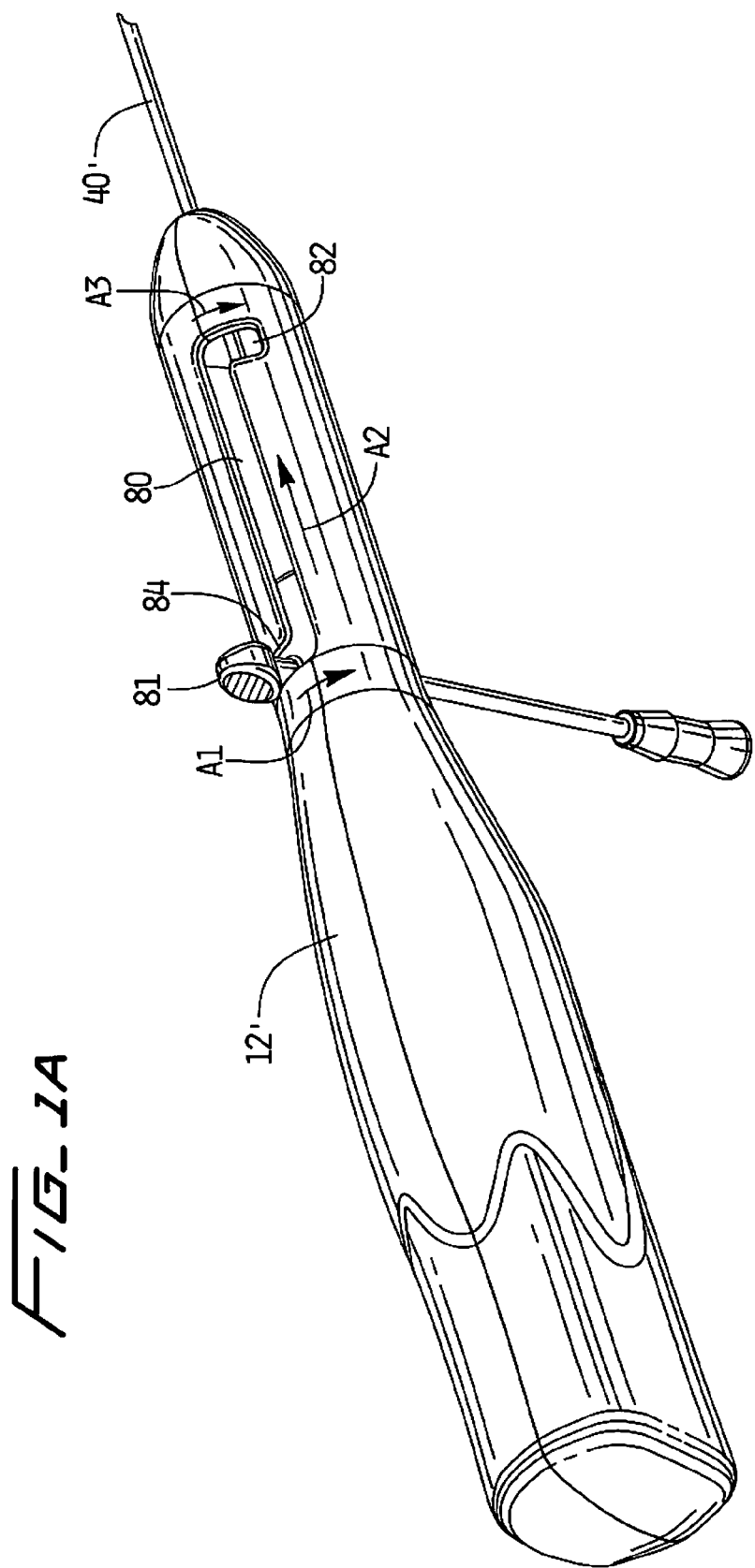
FIG_1A

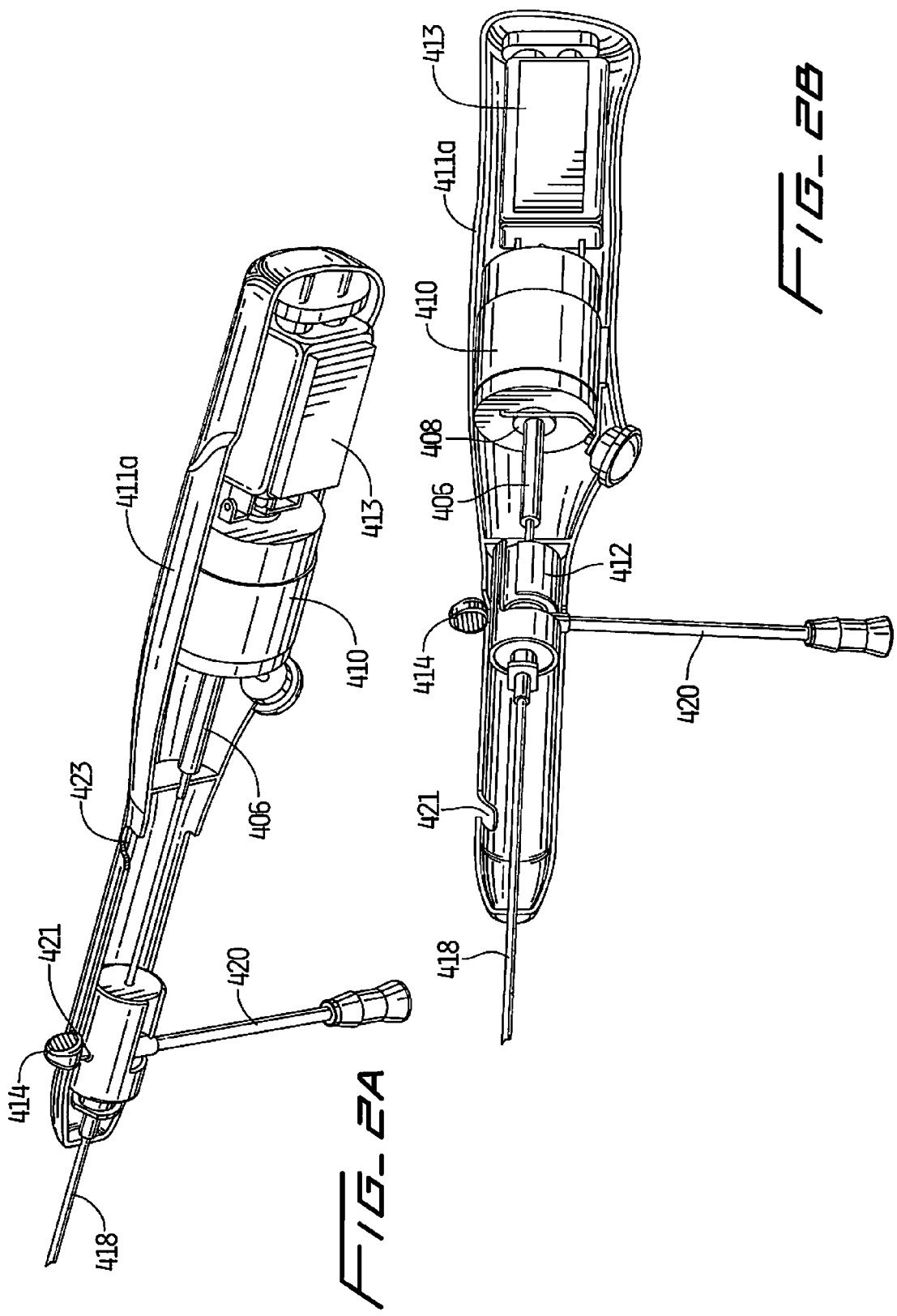

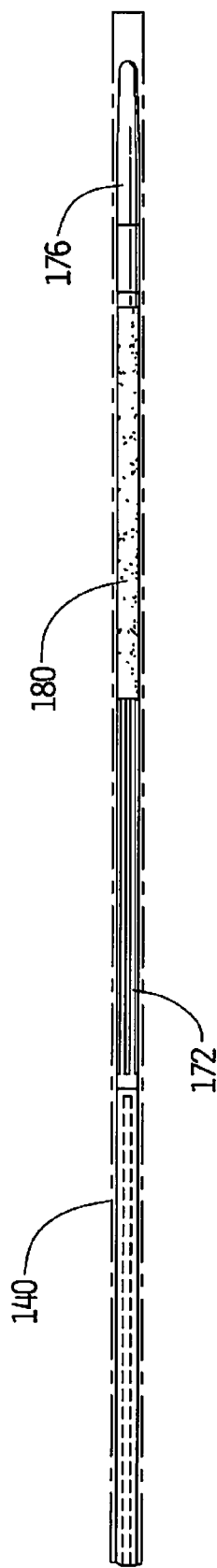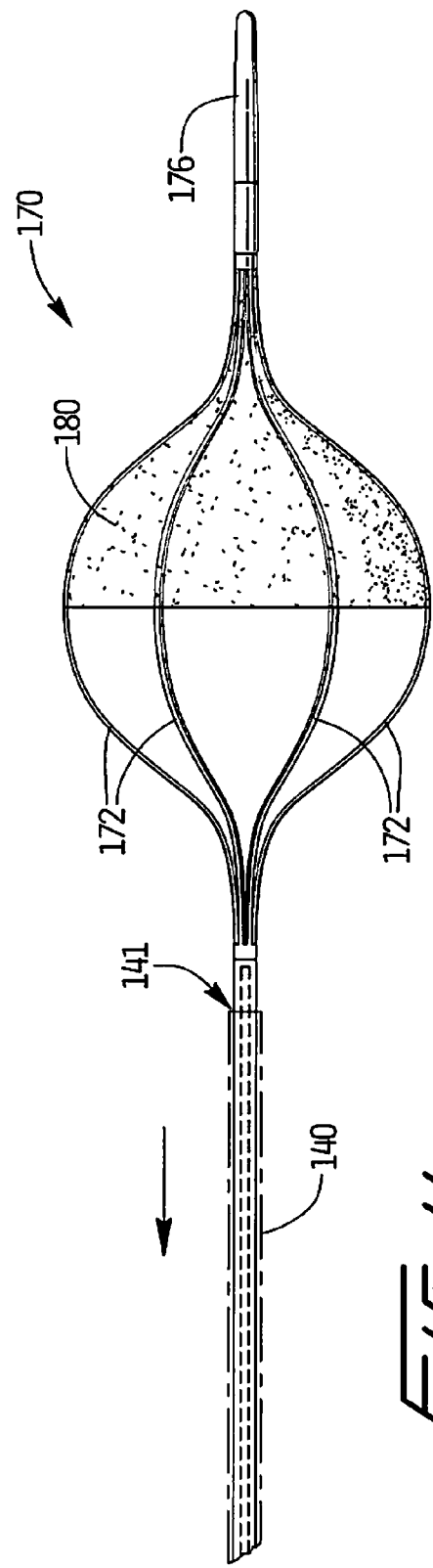

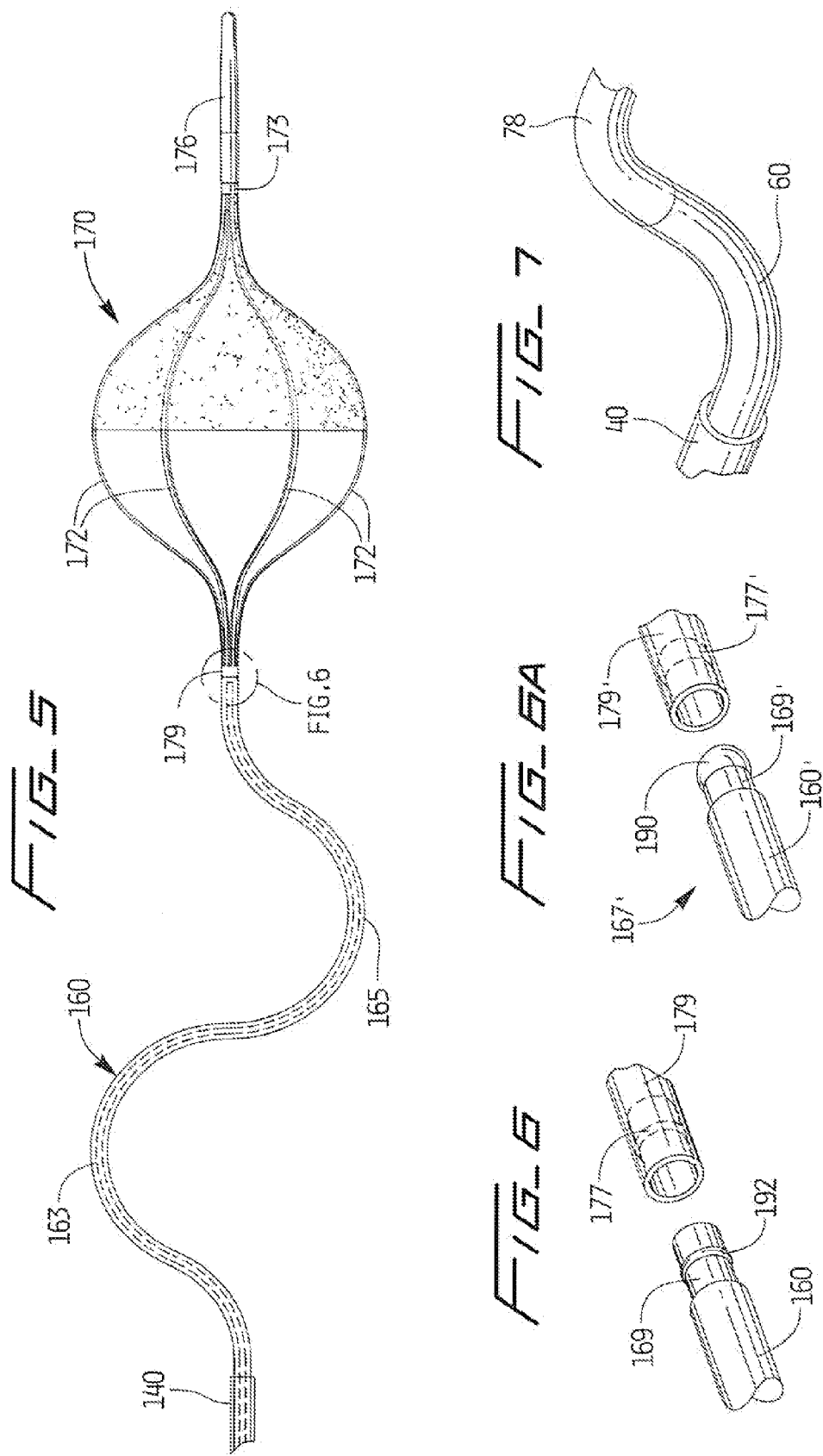

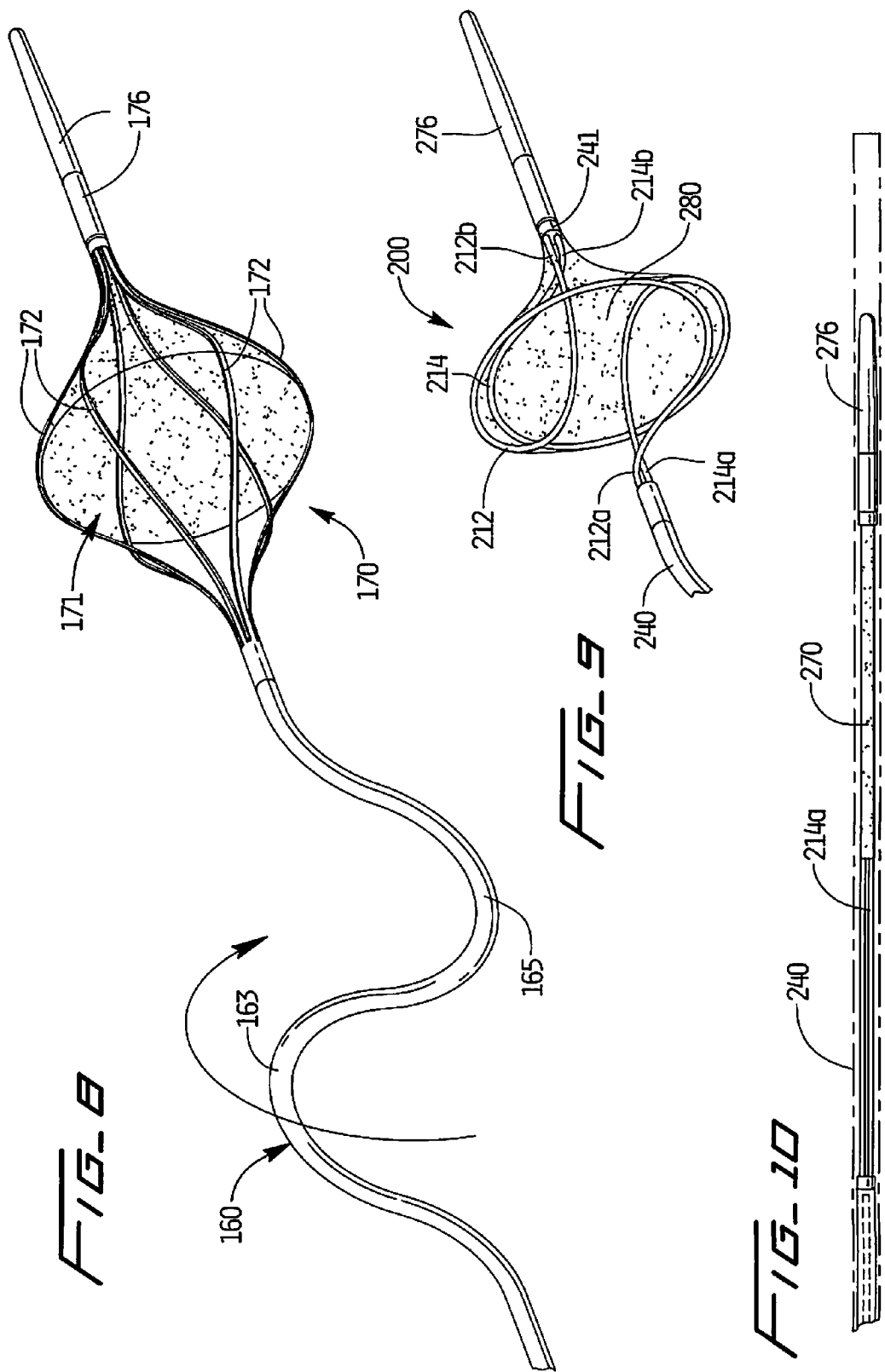

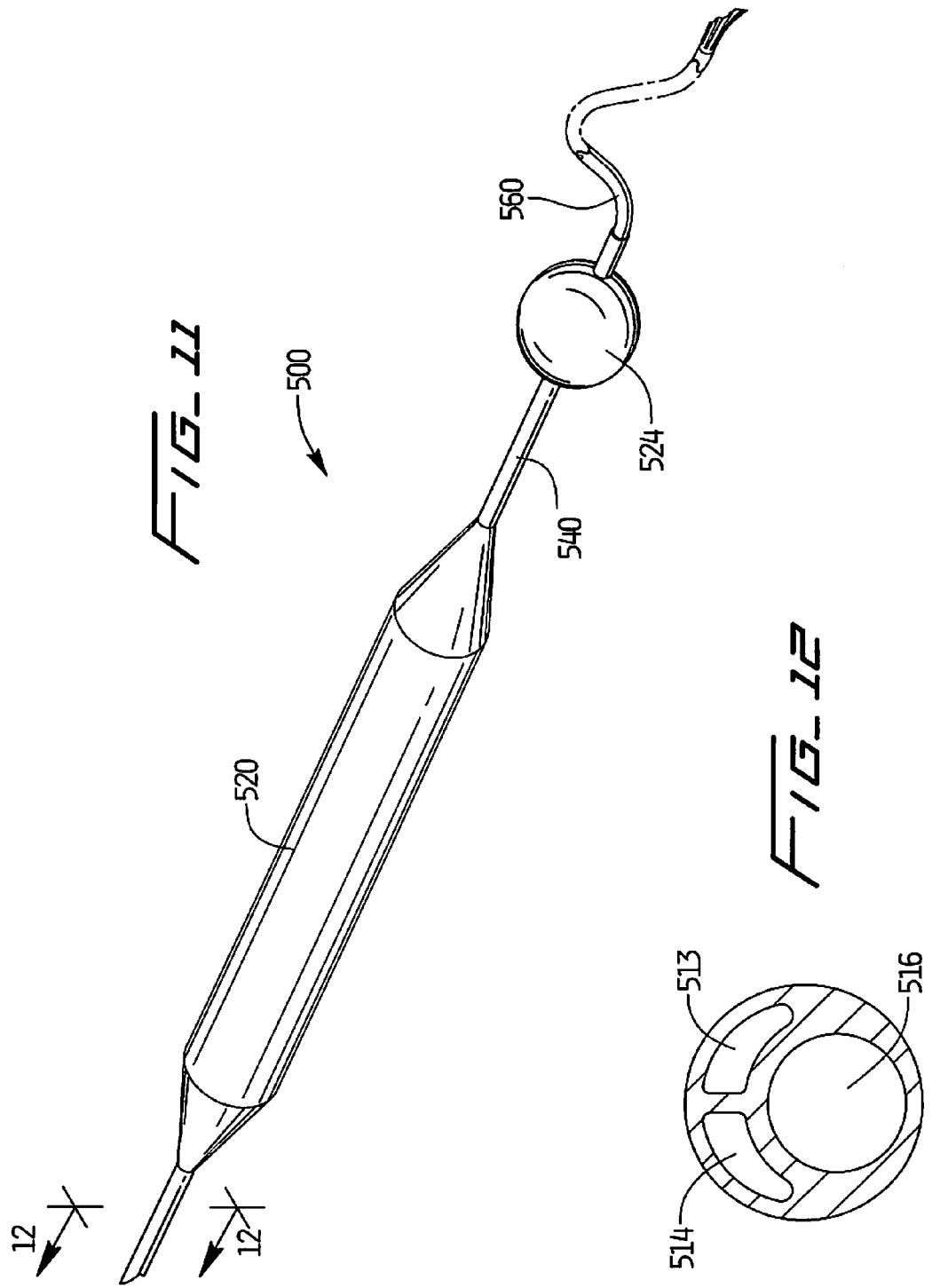

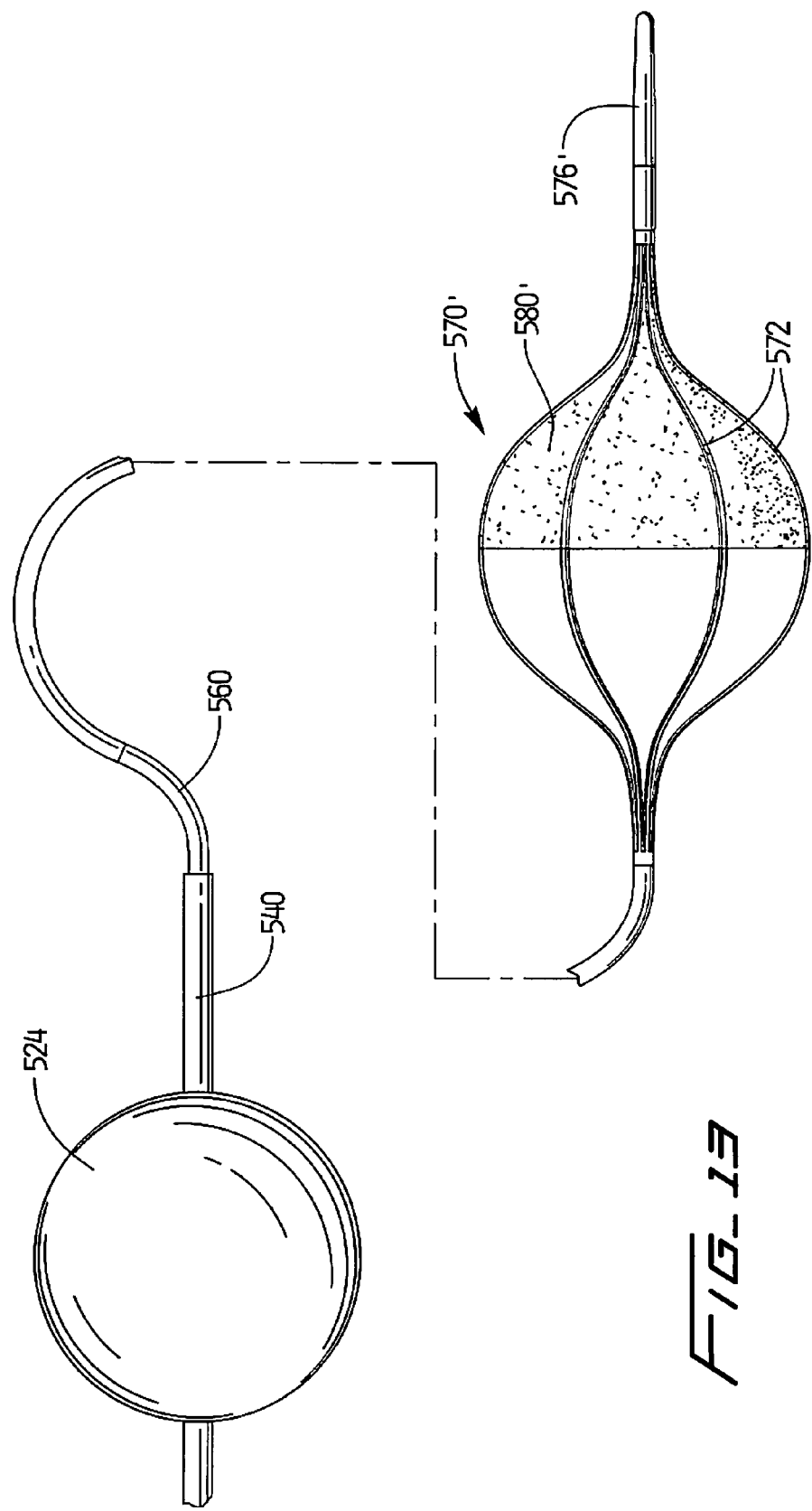
FIG_13

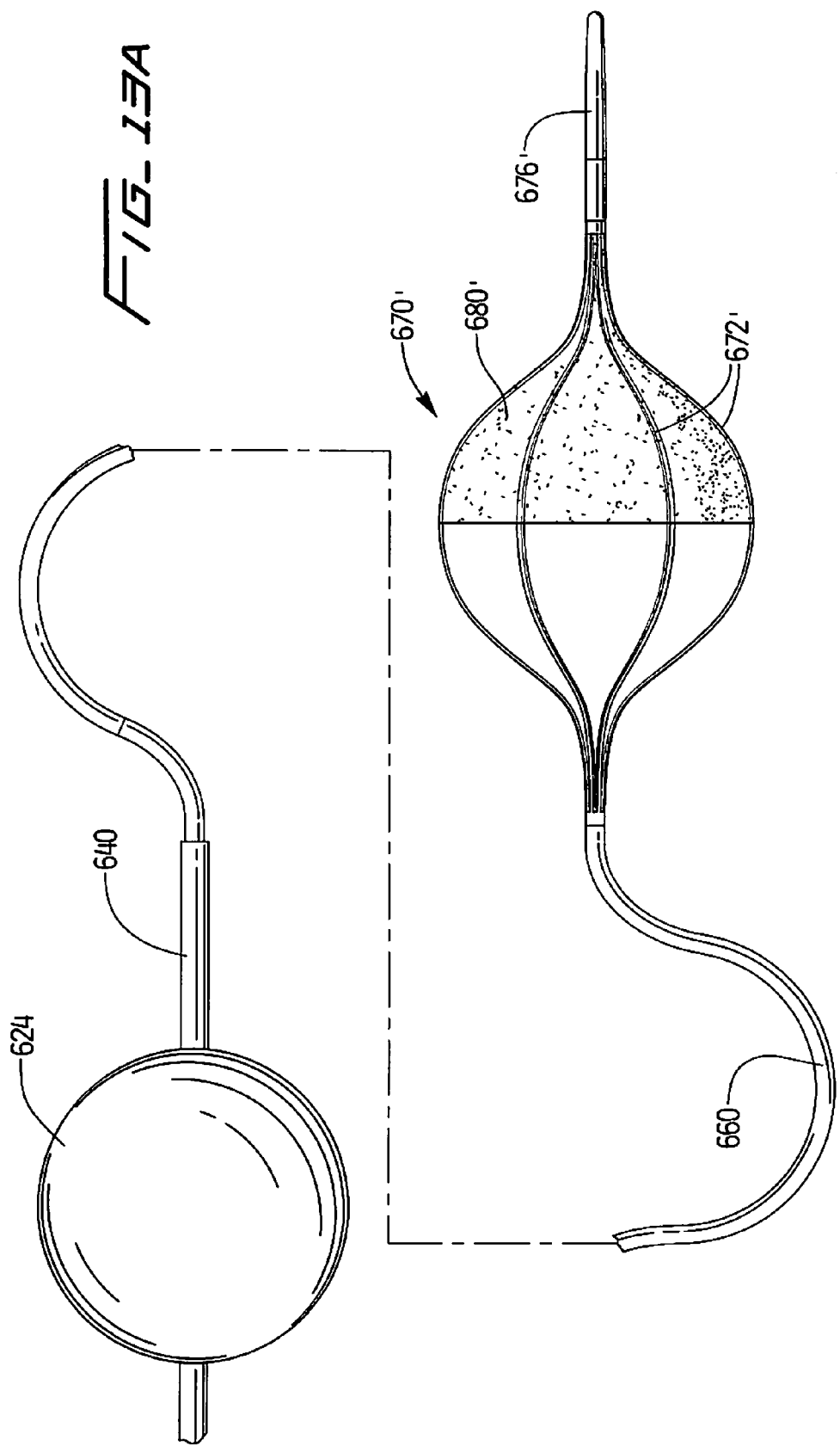

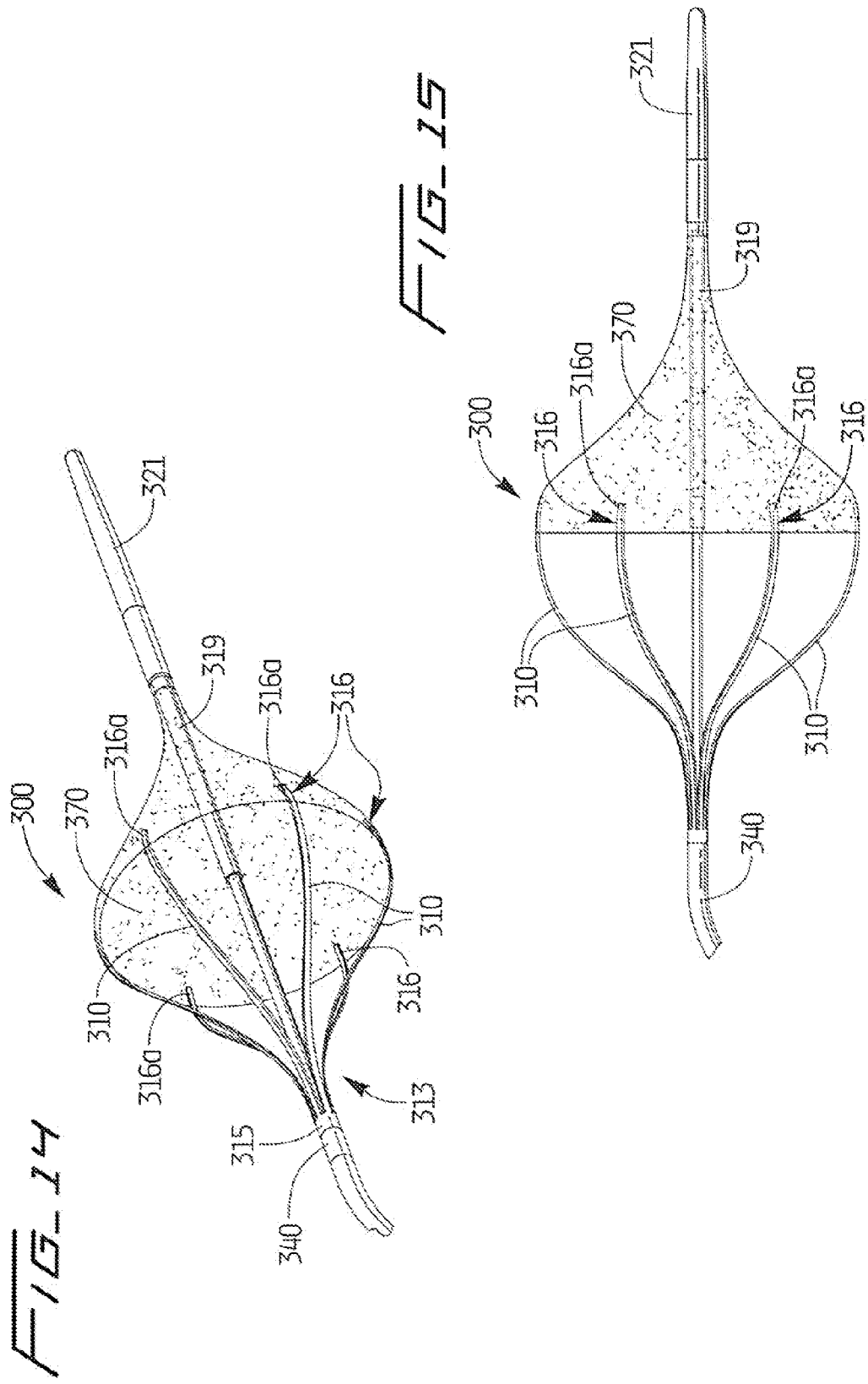

FIG_16
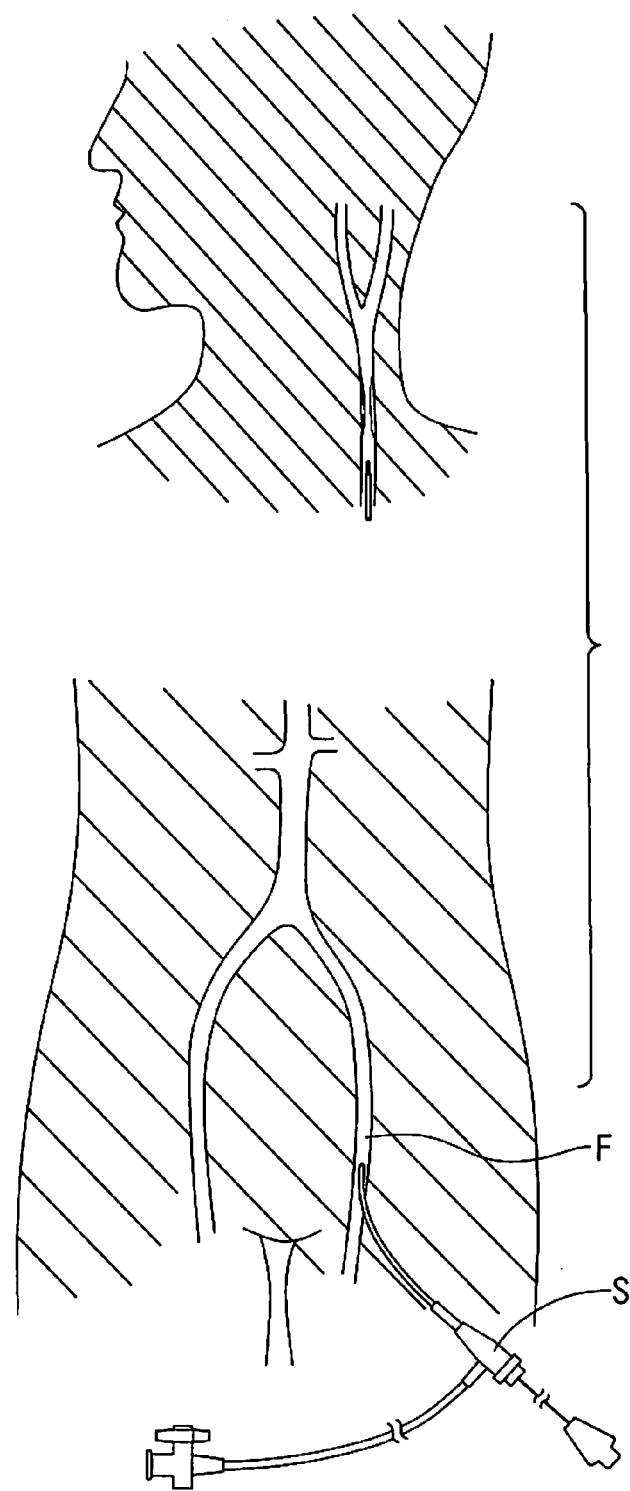

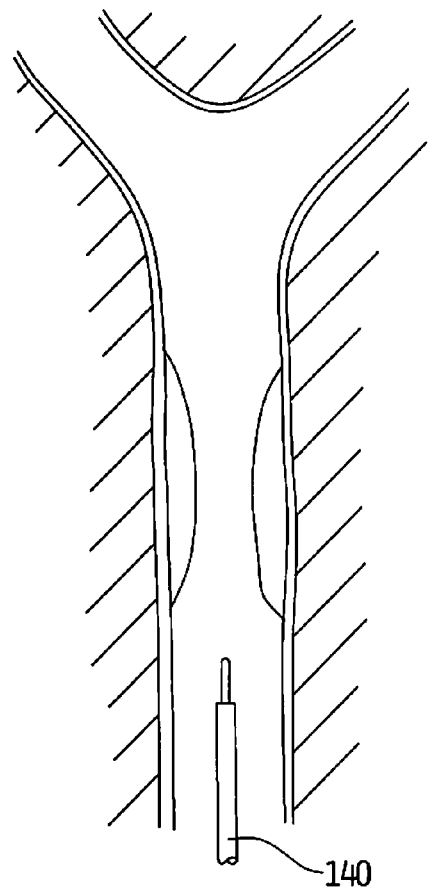
FIG_17
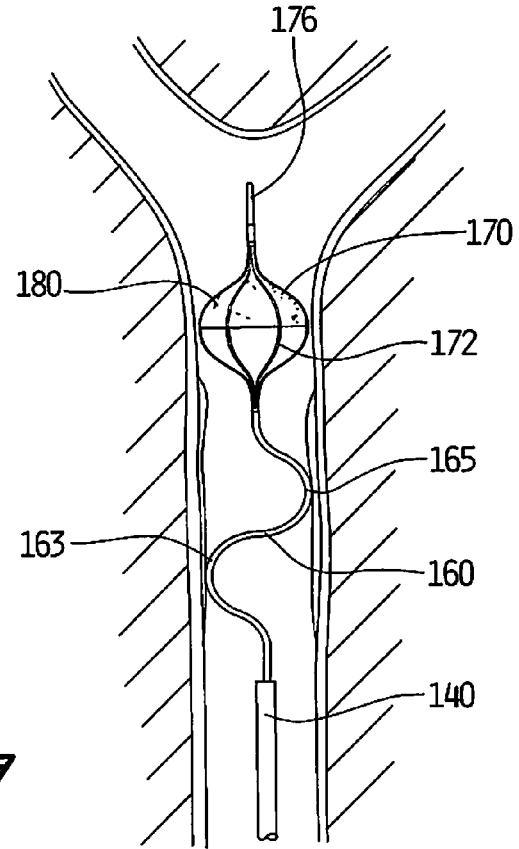
FIG_18

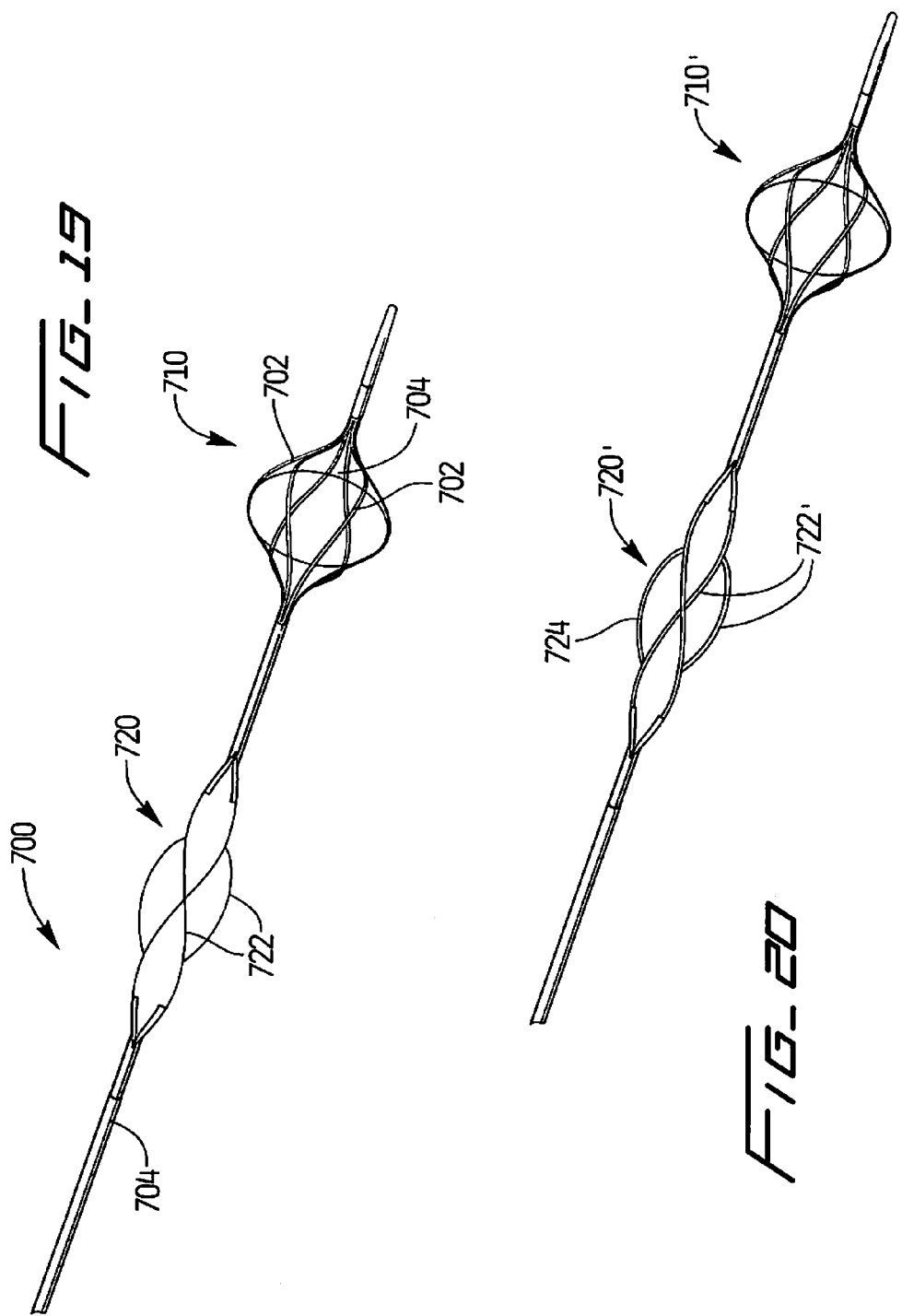

ROTATIONAL THROMBECTOMY WIRE WITH BLOCKING DEVICE

This application is a continuation in part of U.S. patent application Ser. No. 12/631,787, filed Dec. 4, 2009 now U.S. Pat. No. 7,909,801, which is a continuation of U.S. patent application Ser. No. 11/267,379, filed Nov. 4, 2005 now U.S. Pat. No. 7,645,261, which is a continuation of U.S. patent application Ser. No. 09/888,149, filed Jun. 22, 2001 now abandoned, which is a continuation in part of Patent Cooperation Treaty Application No. PCT/US00/41355, filed Oct. 20, 2000, which designates the United States, priority from the filing date of which is hereby claimed under 35 U.S.C. §120, which PCT application claims the benefit of U.S. Provisional Patent Applications No. 60/214,331 filed Jun. 27, 2000, and No. 60/161,124 filed Oct. 22, 1999, the benefit of which is hereby claimed under 35 U.S.C. §119. The entire contents of each of these applications are incorporated herein by reference.

BACKGROUND

1. Technical Field

This application relates to a rotational thrombectomy wire for clearing thrombus from native vessels.

2. Background of Related Art

There have been various attempts to break up clots and other obstructing material in the graft. One approach is through injection of thrombolytic agents such as urokinase or streptokinase. These agents, however, are expensive, require lengthier hospital procedures and create risks of drug toxicity and bleeding complications as the clots are broken.

Other approaches to breaking up clots involve mechanical thrombectomy devices. For example, U.S. Pat. No. 5,766,191 discloses a cage or basket composed of six memory wires that expand to press against the inner lumen to conform to the size and shape of the lumen. This multiple wire device is expensive and can be traumatic to the graft, possibly causing damage, since as the basket rotates, the graft is contacted multiple times by the spinning wires. Other risks associated with the basket include the possibility of catching onto the graft itself and tearing the graft as well as catching and tearing the suture at the anastomotic site. Additionally, the basket can become filled with a clot which would then require time consuming withdrawal of the basket, cleaning the basket and reinserting it into the lumen. This device could be traumatic if used in the vessel, could denude endothelium, create vessel spasms and has the potential for basket and drive shaft fracture.

U.S. Pat. No. 6,090,118, incorporated herein by reference in its entirety, discloses a wire rotated to create a standing wave to break-up or macerate thrombus. The single wire is less traumatic than the aforedescribed basket device since it minimizes contact with the graft wall while still effectively mechanically removing thrombotic material.

U.S. Pat. No. 7,645,261, the entire contents of which are incorporated herein by reference, discloses a thrombectomy device having a double balloon structure. This device advantageously reduces the number of individual catheters required to perform the thrombectomy procedure and reduces the number of surgical steps, thus simplifying the procedure and reducing operating costs.

U.S. Pat. No. 7,037,316, the entire contents of which is incorporated herein by reference discloses another example of a rotational thrombectomy wire for breaking up clots in grafts. The thrombectomy wire has a sinuous shape at its distal end and is contained within a sheath in a substantially straight non-deployed position. When the sheath is retracted, the distal portion of the wire is exposed to enable the wire to return to its non-linear sinuous configuration. The wire is composed of two stainless steel wires wound side by side with an elastomeric tip at the distalmost end. Actuation of the motor causes rotational movement of the wire, creating a wave pattern, to macerate thrombus. Thus, it provides the additional advantages of increased reliability and consistency in creating the wave pattern since the wave pattern created by the standing wave of the '118 patent will depend more on the rotational speed and the stiffness of the wire. Additionally, the sinuous configuration enables creation of a wave pattern at a lower rotational speed.

Although the sinuous wire of the '316 patent is effective in proper clinical use to macerate thrombus in dialysis grafts, it is not best suited for use in native vessels. US patent publication no. 2006/0106407, the entire contents of which are incorporated herein by reference, discloses a thrombectomy wire better suited for use in native vessels, and can also be used for deep vein thrombosis and pulmonary embolisms.

In certain thrombectomy procedures, such as in neurovascular or pulmonary procedures, during wire rotation, broken plaque particles which are dislodged can travel through the vascular system. If these particles are too large, then they can create risks for the patient as they travel downstream through the vessels, causing clots which can result in stroke or in certain instances death of the patient. It would be advantageous to reduce these risks in these procedures.

SUMMARY

The present invention advantageously provides a rotational thrombectomy apparatus for breaking up thrombus or other obstructive material in a lumen of a vascular graft or vessel. The apparatus comprises a wire relatively movable with respect to a flexible sheath and has a first configuration and a second deployed configuration, the wire having a straighter configuration in the first configuration. The wire is operatively connected to a motor for rotation of the wire to contact and break up the thrombus or other obstructive material. A blocking device at a distal portion of the apparatus is movable between a collapsed configuration and an expanded configuration, the blocking device in the expanded configuration configured to block thrombus dislodged by rotation of the wire.

In some embodiments, the wire is sinuous in configuration and assumes its sinuous configuration when in the deployed configuration. The wire can be composed of an inner core and an outer coil. In some embodiments, the wire terminates in a C or J-tip wherein rotation creates at least one vibrational node.

Preferably, the wire spins independent of the blocking device such that the blocking device remains substantially stationary (non-rotational) during rotation of the wire.

The blocking device preferably includes a shaft or tubular portion connected to a distal end of the wire wherein the wire is rotatable independent of the shaft or tubular portion.

The apparatus can include one or two inflatable balloons, the balloon(s) spaced proximally of a distal tip of the wire. One balloon can be an angioplasty balloon and one balloon can be configured for engaging and pulling an arterial plug. In some embodiments, the first balloon is positioned proximal of the second balloon.

The apparatus can includes a housing, wherein the wire extends from the housing and the housing preferably further includes a battery and a motor for causing rotation of the wire.

In some embodiments, the blocking device includes a plurality of wires and a porous material covering at least a portion of the wires. The material in some embodiments covers only a distal portion of the wires. In some embodiments, the material covers the entire portion of the wires. The material can be attached to an outer surface and/or inner surface of the wires. In some embodiments, the wires are expandable to expand a material overlying the wires.

In another aspect, the present invention provides a thrombectomy apparatus for breaking up thrombotic material comprising a rotatable wire having a non-linear configuration, a blocking device positioned at a distal portion of the wire distal of the non-linear configuration to expand radially with respect to the wire, and a motor for rotating the wire to break up thrombotic material as the wire rotates about its axis.

The apparatus can include a flexible tube with the wire rotatable with respect to the flexible tube. Preferably, the wire is rotatable independent of the blocking device.

In another aspect, the present invention provides a method for breaking up the thrombotic material from a lumen of a vascular graft or vessel comprising:

inserting a sheath;

exposing a rotatable wire of a thrombectomy apparatus from the sheath;

rotating the wire to break up thrombotic material; and blocking at least some of the thrombotic material with a blocking device connected to a distal portion of the apparatus.

In some embodiments, the step of exposing a rotatable wire from the sheath changes the shape of the wire. In some embodiments, the step of rotating the wire includes the step of rotating the wire while the blocking device does not rotate.

Preferably, the blocking device is movable between a collapsed and expanded position.

BRIEF DESCRIPTION OF THE DRAWINGS

Preferred embodiment(s) of the present disclosure are described herein with reference to the drawings wherein:

FIG. 1 is a perspective view of a first embodiment of a thrombectomy apparatus of the present invention;

FIG. 1A is a perspective view of an alternate housing having a locking slot for the flexible sheath;

FIG. 2 is a perspective view of a distal portion of an alternative embodiment of a thrombectomy apparatus of the present invention;

FIGS. 2A and 2B are perspective and side views, respectively of a proximal portion of the apparatus of FIGS. 1 and 2 with a housing half removed to illustrate the internal components;

FIG. 3 is a side view illustrating the blocking device of FIG. 2 in a collapsed position within the sheath;

FIG. 4 is an enlarged side view of the blocking device of FIG. 2 in the expanded (deployed) position exposed from the sheath as the sheath is retracted;

FIG. 5 is an enlarged side view of the thrombectomy wire and the blocking device of FIG. 2 in the deployed position exposed from the sheath as the sheath is further retracted;

FIG. 6 is a perspective view illustrating an embodiment of the attachment of the blocking device of FIG. 2 to the thrombectomy wire;

FIG. 6A is a perspective view illustrating a second embodiment of the attachment of the blocking device of FIG. 2 to the thrombectomy wire;

FIG. 7 is a perspective view of the area of detail of FIG. 1 illustrating an embodiment of the attachment of the blocking device of FIG. 1 to the thrombectomy wire;

FIG. 8 is a perspective view illustrating rotation of the thrombectomy wire of FIG. 2;

FIG. 9 is a perspective view of an alternate embodiment of the blocking device;

FIG. 10 is side view of the device of FIG. 9 in the collapsed position within a sheath;

FIG. 11 is a perspective view of an alternate embodiment of the thrombectomy apparatus of the present invention having two balloons;

FIG. 12 is a cross-sectional view taken along line 12-12 of FIG. 11;

FIG. 13 is an enlarged view of the distal end of the apparatus of FIG. 12, showing the distal balloon in the inflated condition and the blocking device in the expanded position;

FIG. 13A is a side view of another alternate embodiment of the thrombectomy apparatus showing the wire and blocking device of FIG. 2 with a balloon, the balloon and the blocking device shown in the deployed configuration;

FIG. 14 is a perspective view of another alternate embodiment of the blocking device of the present invention;

FIG. 15 is a side view of the blocking device of FIG. 14;

FIGS. 16-18 illustrate one insertion method of the apparatus of FIG. 2 into a carotid artery;

FIG. 19 illustrates an alternate embodiment of the thrombectomy device of the present invention with the blocking device in the deployed position; and FIG. 20 illustrates an alternate embodiment of the thrombectomy device of the present invention with the blocking device in the deployed position.

DETAILED DESCRIPTION OF PREFERRED EMBODIMENTS

Referring now in detail to the drawings where like reference numerals identify similar or like components throughout the several views, FIG. 1 illustrates a first embodiment of the wire of the thrombectomy apparatus of the present invention and FIG. 2 illustrates a second embodiment of the wire of the thrombectomy apparatus of the present invention. Each of the devices of FIGS. 1 and 2 has a particle blocking device at the distal end configured to block large dislodged particles during the thrombectomy procedure to block their travel downstream. In both these embodiments, the blocking device is attached to the wire such that it does not rotate when the wire spins. This is described in more detail below.

The thrombectomy apparatus of FIG. 1 is designated generally by reference numeral 10. The apparatus includes a housing 12 composed of two housing halves 12a, 12b, a flexible tube or sheath 40 and a rotational thrombectomy wire 60 contained within the flexible sheath 40. A knob 42, extending from distal end 14 of housing 12, is attached to the flexible sheath 40 to enable both rotation and sliding movement of the flexible sheath (tube) 40 with respect to the wire 60 which is fixed axially. Note that although the flexible sheath 40 is shown as slidable and the wire 60 is fixed axially, alternatively, the wire can be axially slidable with the sheath 40 stationary, or both the wire 60 and sheath 40 can be slidable. In any case, such relative movement of the wire 60 and sheath 40 will enable the wire 60 to be exposed to assume the curved configuration described below to enable removal of obstructions, such as blood clots, from the lumen of the vascular structure. i.e. the vascular graft or the vessel wall.

It is also contemplated that the wire can be a separate component/assembly insertable into a separate sheath component/assembly either prior to insertion into the body or after the sheath is already placed in the body. In the latter, the sheath can be inserted to the target site over a placement guidewire and then the guidewire removed for insertion of the thrombectomy wire into the already placed sheath. The wire would include a housing containing a motor or attachable to a housing containing a motor either prior to or after insertion through the sheath.

Contained within housing 12 is a motor powered by a battery contained within a compartment in the housing accessible by removing battery door 33. An actuation button is electrically connected to one contact terminal of the battery and the motor is electrically connected to another contact terminal of the battery. The actuation button can be connected to the motor via a wire strip such that depression of the button, which is accessible from a portion of housing 12, turns on the motor to activate the apparatus.

Wire 10 (or wire 100 discussed below) is operatively connected to the motor. Operative connection encompasses direct connection or connection via interposing components to enable rotation when the motor is actuated.

In one embodiment, the wire 60 is operatively connected to the motor via a support tube which is preferably composed of metal. A speed reducing gear can be provided to decrease the rotational speed. When the motor is energized, the support tube is rotated about its longitudinal axis, via rotation of a chuck driven by gears, thereby rotating the wire 60 about its longitudinal axis. This rotation of wire 60 creates at least one vortex that macerates and liquefies the thrombus into small particles within the vascular lumen. Further details of the internal components which can be utilized to connect and rotate the wire are illustrated and described in U.S. Pat. No. 7,507,246, the entire contents of which are incorporated herein by reference. Such arrangement can also be used to connect and spin the thrombectomy wire of the embodiment of FIG. 2 as well as the other embodiments described herein.

As noted above, flexible tube (sheath) 40 is slidable with respect to the housing 12 and wire 60. Flexible tube 40 is also rotatable. Knob 42 can have a gripping region 46. Sliding movement of knob 42 accordingly slides sheath 40 axially and rotation of knob 42 accordingly rotates sheath 40 about its longitudinal axis. Proximal sliding movement of knob 42 exposes rotational wire 60, enabling it to assume its curved configuration; rotation of knob 42 orients the rotational wire 60 due to the J-shaped distal end. The gripping region 46 and/or extension 48 of knob 42 can contain external threads (not shown) for threaded engagement with the distal end of housing 12 to lock the sheath 40 in the advanced and retracted positions to maintain exposure or covering of the wire 60.

As an alternative, a locking slot 80 can be provided as in FIG. 1A. Slot 80 is formed in housing 12'. Post 81 extends radially from the sheath 40' and is movable radially into radial slot portion 82 of elongated axial slot 80 to a locking position or movable radially into radial slot portion 84 of elongated slot 80 to another locking position to respectively retain the sheath 40' in its advanced position to cover the wire 60 or retracted position to expose the wire 60. Such locking post/slot arrangement can also be used to uncover and cover wire 160 in the alternate apparatus of FIG. 2 as well as the other wires disclosed herein. Thus, to advance the sheath 40' to cover the wire 60, post 81 would be moved radially in the direction of arrow A1, slid axially in slot 80 in the direction of arrow A2, and then moved radially into slot portion 82 in the direction of arrow A3. To retract and lock the sheath 40' to expose wire 60, the post 81 would be moved in the reverse direction into radial slot portion 84.

The flexible sheath 40 can optionally contain one or more braided wires embedded in the wall to increase the stiffness. Such braided wires could preferably extend the length of the sheath 40.

It is also contemplated as noted above that the thrombectomy wires disclosed herein can be provided without a sheath and inserted into or an already placed sheath in the body or inserted into a sheath and then together placed in the body.

Extension arm 52 of the Touhy borst positioned within housing 12 has a lumen communicating with the lumen of flexible sheath 40. Fluids such as imaging dye can be injected through arm 52, flowing through sheath 40 in the space between wire 60 and the inner wall of the sheath 40, and exiting a distal opening to flow into the graft or vessel. This imaging dye can be used to provide an indication that fluid flow has resumed in the graft or vessel. The Touhy can contain a conventional silicone gasket which is compressed when tightened to provide a seal to prevent back flow of fluid around the support tube. A radiopaque marker can be provided in the apparatus for imaging to visually locate the position of the apparatus. Such extension arm connection and structure can also be utilized with the FIG. 2 embodiment such that fluid can exit distal opening 141 (see FIG. 4).

An alternate wire connection is illustrated in FIGS. 2A and 2B with one of the housing halves removed to illustrate the internal components. Coupler 406 having a washer 408 extends from motor 410 (powered by battery 413) which is seated within housing half 411a. Slide 412 has post 414 extending therefrom for access through the housing for the user to advance and retract the sheath 418. Post 414 locks the sheath in an advanced position (FIG. 2A) and a retracted position as it engages respective distal or proximal slot 421, 423. Extension arm 420 enables fluid injection through sheath 418.

Referring back to FIG. 1, the wire 60 terminates in a J-tip configuration at region 61. Due to this angle, when the wire is rotated by the motor at sufficient speed, at least one vibrational node is formed. Details of this J-tip wire are described in U.S. Pat. No. 6,090,118, the entire contents of which are incorporated herein by reference. This patent also describes creation of a standing wave.

A clot blocking device in the form of a basket 70 is connected to the wire 60. The device can also be configured to capture the clots. The basket 70 has a proximal portion 72 and a distal portion 74. Proximal portion converges into tubular portion 71 and distal portion 74 converges into tubular portion 73. Distal tubular portion 73 includes a soft atraumatic tip 76 attached thereto which can be composed of rubber, Pebax or other elastomeric materials to provide an atraumatic distal end to prevent damage to the vessel wall during manipulation. The proximal portion 72 has a curved tube 78 (either integral or attached) which is configured for connection to a distal portion of wire 60. Various methods of attachment can be utilized. The attachment methods enable the wire 60 to spin while the blocking device does not spin and remains substantially stationary. One example of an attachment structure is shown, in FIG. 7 wherein wire 60 can have an O-ring positioned thereover which is seated within a recess (as in the embodiment 6 of FIG. 6 described below) of curved connector tube 78 of blocking device 70. This attachment allows the wire 60 to spin inside the lumen of the tube 78. Other attachments for independent rotation are also contemplated. The curved tube 78 is configured so that a central longitudinal axis of the blocking device 70 is substantially aligned with a central longitudinal axis of the thrombectomy catheter 10. That is, the tube bends in a U-shape so a distal end 79 of the tube is aligned with sheath 40 and with the proximal tubular portion 71 of blocking device 70.

The blocking device 70 is movable between an initial collapsed position within the sheath 40 for delivery and an expanded deployed configuration when exposed from the sheath. Such collapsed and expanded positions are shown in FIGS. 3 and 4 in conjunction with the wire 160 of FIG. 2 which is applicable to the blocking device 70 of FIG. 1 as FIGS. 1 and 2 differ in the configuration of the wire, but have the same blocking device. More details of the blocking device are discussed below.

Turning to the alternate embodiment of the wire of FIG. 2, the rotational thrombectomy wire 160 in its expanded (deployed) configuration assumes a substantially sinuous configuration. This sinuous configuration resembles a sine curve.

Wire 160 has a substantially linear portion extending through most of its length, from a proximal region, through an intermediate region to distal region 166. At the distal region 166, wire 160 has a sinuous shape in that as shown it has a first arcuate region 163 facing a first direction (upwardly as viewed in the orientation of FIG. 5) and a second arcuate region 165, spaced longitudinally from the first arcuate region 163, facing a second opposite direction (downwardly as viewed in the orientation of FIG. 5). These arcuate regions 163, 165 form "peaks" to contact vascular structure as the wire 160 rotates. The distal tip of wire 160 can continue upwardly as a continuation of the "sine curve" configuration. An atraumatic tip 176, preferably composed of rubber, Pebax, or other elastomeric materials, although other materials are also contemplated, is inserted, molded or otherwise attached to the distalmost tip (e.g. distal tubular portion 173 formed at the distal converging region) of the blocking device 170 to provide the apparatus 100 with an atraumatic distal tip to prevent damage to the graft or vessel wall during manipulation of the wire 160 and blocking device 170.

When the sheath (tube) 140 is in the advanced position as in FIG. 3, the curved regions of the wire 160 are compressed so the wire 160 (including the distal region 166) is contained in the flexible sheath 140 in a substantially straight or linear non-deployed configuration. The capturing device 170 is also in a substantially straight position within the sheath 140 in the initial position. This covering of the wire 160 and device 170 by sheath 140 facilitates insertion through the introducer sheath and manipulation within the vascular structure. When the sheath 140 is retracted by proximal axial movement of the knob (in the same manner as knob 42 of FIG. 1) or by the post 81 in the FIG. 1A or 2A embodiment, the blocking device 170 and the distal region 166 of the wire 160 are exposed to enable the blocking device 170 to return to its expanded configuration and enable wire 160 to return to its non-linear sinuous configuration shown in FIGS. 2 and 5. The wire 160 is preferably composed of stainless steel which is pre-bent to the curved configuration of FIG. 5 and returns to this position when released from the flexible sheath 140.

In one embodiment, the wire 160 is composed of an inner core and outer layer or coil. The inner core can be formed by twisting a series of wires together in a tight configuration. The outer coil can be formed by winding a wire, preferably of larger diameter, to form an opening therethrough. This tightly wound outer/inner core structure enables rotation of the distal end of the wire 160 corresponding to rotation at its proximal end as torque is transmitted to the distal end.

Various dimensions of the wire and flexible tube are contemplated. By way of example only, in one embodiment, where the flexible tube 140 has an outer diameter of about 0.062 inches, the curved regions of the wire 160 would extend from the longitudinal axis a distance of about 0.188 inches and the radius of curvature at region 165 would be about 0.376 inches in a wire having an overall diameter (combined outer coil and inner core) of about 0.035 inches. As can be appreciated, these dimensions are provided by way of example as other dimensions are also contemplated.

In an alternate embodiment of the sinuous thrombectomy wire, the wire includes a core, a bifilar wire (coil), and shrink wrap. The core can be formed by multiple twisted wires. The bifilar wire can be formed by two wires wound together, and wound side by side so the cross-sectional area or diameter of the wire fills the space between adjacent turns of the other wire. The distal region of the bifilar wire is formed into a sinuous or s-shape to contact the vessel wall as the wire rotates. Although in the preferred embodiment the outer wire is a multifilar wire in the form of a bifilar wire (two wires), a different number of wires could be wound to form the outer wire component of the thrombectomy wire, including a single wound wire.

In this embodiment, the core is positioned within the bifilar wire and preferably has an outer diameter substantially equal to the inner diameter of the coil. The core has a sinuous shaped portion within the sinuous shaped portion of the outer wire, corresponding to the sinuous shape. In one embodiment, the core extends the entire length of the bifilar wire. The core can alternatively have a length of about 4-5 inches so it extends through the distal linear portion and sinuous portion of the wire.

The core in this embodiment can be composed of a flexible material which will limit the compressibility of the wire during use. The core can be composed of Nylon, and preferably a drawn Nylon monofilament. Other possible materials include, for example, Teflon, polypropylene, PET, and fluorocarbon as well as shape memory material such as Nitinol. The Nylon provides a non-compressible material to limit the compressibility of the wire during use. This enables the coil (bifilar wire) to compress only to that diameter. By limiting compressibility it strengthens the wire as it reduces its degree of elongation if it is under torque. It also prevents bending or knotting of the wire which could otherwise occur in native vessels. It increases the torsional strength of the wire and also strengthens the wire to accommodate spasms occurring in the vessel. The core can be attached by adhesive at the tip, welded, crimped, soldered or can alternatively be free floating.

A shrink wrap material can cover a distal portion of the bifilar wire to block the interstices of the coil and provide a less abrasive surface. The shrink wrap can be made of PET, Teflon, Pebax, polyurethane or other polymeric materials. The material can extend over the exposed portion of the wire (preferably for about 3 inches to about 4 inches) and helps to prevent the native vessel from being caught in the coil and reduces vessel spasms. Alternatively, instead of shrink wrap, a coating can be applied to the coil formed by the bifilar wire to cover the interstices. (Examples of coatings which can be utilized include hydrophilic coatings and PTFE.)

In the embodiment of a core of shape memory material, the memorized configuration is sinuous or s-shape substantially corresponding to the s-shape of the bifilar wire. In the softer state within the sheath, the core is in a substantially linear configuration. This state is used for delivering the wire to the surgical site. When the wire is exposed to warmer body temperature, or when released from the constraints of the sheath, the core transforms to its austenitic state, assuming the s-shaped memorized configuration.

The Nitinol core, like the Nylon core, is not compressible so it will also limit the compressibility of the bifilar wire. The Nitinol core also will increase the stiffness of the wire thereby reducing the chance of knotting and kinking and increase the strength of the wire to accommodate any spasms in the vessel. Its shape memory helps hold the amplitude of the bifilar wire during use to maintain its force against the clot for maceration upon rotation. It preferably extends about 4-5 inches so it extends through the distal linear portion and sinuous portion of the wire. It can alternatively extend a shorter or longer length within the wire, or even the entire length.

In another embodiment, a stainless steel braid, cable, or strand of wires twisted together provides the inner core member to limit compressibility of the coil (bifilar wire) and provide increased stiffness, strength and other advantages of the core enumerated above.

Further details of the wire are disclosed in pending Patent Publication No. 2006/0106407 published May 18, 2006, the entire contents of which are incorporated herein by reference.

Turning now to the clot blocking device, the blocking device will now be described in conjunction with FIGS. 2-5 and 8, which show the sinuous wire configuration. It should be understood that the same clot blocking devices can be used with the J-wire embodiment of FIG. 1, however, for brevity, only its use with the sinuous wire of FIG. 2 will be described in detail.

The blocking device 170 is positioned distally of the thrombectomy wire 160 and is therefore exposed before the wire during use. The device 170 includes a plurality of wires 172. The wires 172 are movable from a compressed configuration, positioned inside the sheath 140 (FIG. 3), to an expanded configuration when exposed from the sheath as shown in FIG. 4. The wires 172 extend longitudinally and expand radially when released from the sheath 140 and can be made of a material with sufficient springiness or alternatively made of shape memory material with a memorized expanded configuration. A membrane 180 with pores of sufficient size to allow blood flow therethrough but small enough to block thrombus or other particles which could pose a risk to the patient covers the wires 170. The membrane 180 can cover the entire "cage" or "basket" formed by the wires 172 or optionally can be disposed only over a region of the wires 172, such as the distal half as shown in FIG. 4. Also, the membrane 180 can be attached to an outer surface and/or an inner surface of the wires 172. As shown, the wires 172 expand radially with respect to a longitudinal axis of the catheter. Although six wires are shown, a different number of wires could be provided to support the membrane 180.

The blocking device 170 (as well as the alternate blocking devices 200, 300 described below) can be utilized with any of the rotational thrombectomy wires described herein as well as with other thrombectomy devices to block particles dislodged during the thrombectomy procedure.

FIG. 6 illustrates one embodiment of attachment of the capturing device 170 to wire 160 to enable independent rotation of the thrombectomy wire 160. The distal end of wire 160 has an O-ring 192 configured to be seated within a groove 177 in proximal tubular portion or shaft 179 of blocking device 170. Note the wire 160 in this embodiment steps down to form reduced diameter region 169 to accommodate the O-ring 192 to maintain the diameters of the wire 160 and tubular portion 179 substantially flush. Such groove engagement enables wire 160 to spin without spinning the blocking device 170.

FIG. 6A illustrates an alternate attachment configuration. The distal end 167' of wire 160' terminates in a ball tip 190 which is seated within groove 177' of proximal tubular portion or shaft 179' of blocking device 170 to enable the wire 160 to spin within tubular portion 179' without spinning the blocking device 170. Other connections to achieve rotation are also contemplated. Note wire 160 steps down to form a reduced diameter region 169'.

In the alternate embodiment of FIG. 9, blocking device 200 includes two looped wires 212, 214. In the collapsed configuration of FIG. 10, the wires 212, 214 are in an elongated position substantially parallel with the longitudinal axis of the catheter. The wires 212, 214 are maintained in this configuration by the sheath 240. The membrane 280 is attached to the wires either to an outer surface and/or an inner surface and can be attached to cover only a portion, e.g. the distal portion, or the entire portion of the wires 212, 214. Although two wires are shown, more wires could be provided. Also, alternatively a single wire could be provided.

When the blocking device 200 is exposed from the sheath 240, the wires 212, 214 automatically move to their expanded position to form loops. The wires can be made of springy material or shape memory material. Ends 212a, 214a extend distally from proximal tubular portion 240 and ends 212b, 214b extend proximally from distal tubular portion 241. That is, a first looped wire region is formed by each wire 212, 214 on one side of a longitudinal axis of the apparatus and a second looped wire region is formed by each wire 212, 214 on the other side of the longitudinal axis of the apparatus, preferably about 180 degrees apart. This double looped configuration causes the membrane 280 to be stretched on opposing sides of the device and preferably block about a 360 degree area. Thus, the stretching of membrane 280 on both sides of the device to the illustrated expanded configuration of FIG. 9 blocks the flow of select material. The membrane 280 preferably has pores to provide openings for blood flow, with the membrane 280 blocking flow of materials exceeding the pore size.

The expanded loops of the wires 212, 214 thus lie in a plane at an angle to both the longitudinal axis and transverse axis of the apparatus (catheter). In other words, the plane of the loop opening would be at an angle (preferably at a slight angle) to the longitudinal and transverse axis of the sheath 240. The wires 212, 214 would thus extend such that the loop opening is slightly offset from the direction of the longitudinal axis of sheath 240 but still open generally in the direction of blood flow. That is, a central longitudinal axis extending through the loop opening would be at an angle with respect to the longitudinal axis of the sheath 240. Alternate wire loops and membranes are disclosed in commonly assigned U.S. Pat. Nos. 7,604,649 and 7,331,976, the entire contents each of which are incorporated herein by reference. For example, the wire can be configured so the two looped sections are axially offset as shown in FIG. 28 of U.S. Pat. No. 7,604,649.

Consequently, in some embodiments, the plane of the loop opening is perpendicular to the longitudinal axis of the catheter (parallel to the transverse axis) and perpendicular to the direction of blood flow. In other embodiments, rather than perpendicular, the plane of the loop opening is at an angle less than 90 degrees, but preferably greater than about 45 degrees to the longitudinal axis.

The expansion movement of the wires causes the overlying membrane to be deployed, moving to an expanded position. The membranes 180 (and 80, 280 and 380 discussed herein) can be a polymeric membrane, such as polyurethane or PET, which is expanded by the wires. A mouth or opening e.g. opening 171 of FIG. 8 can be provided at the proximal end of the membrane. The polymeric material would have small holes or windows dimensioned for allowing blood flow while blocking embolic material. Thus, embolic material exceeding a certain size carried by the blood is blocked with smaller particles flowing through the holes or pores in the membrane.

Alternatively, the blocking device can be a tightly wound metal braided material such as shape memory metal, e.g. Nitinol.

To withdraw the blocking device, the sheath and/or wires are moved to retract the loop and membrane to the initial low profile insertion position within the sheath 240.

Another alternate embodiment of the blocking device is designated by reference numeral 300 in FIGS. 14 and 15. The device has a plurality of wires 310 extending distally from proximal tubular portion 315 at converging end 313 and terminating in free ends 316. The tips 316a of the wires 310 can curve slightly radially inwardly as shown. Although six wires are shown, a different number of wires can be provided. The membrane 370 is positioned over the wires 310 but can alternatively be attached to an inner surface of wires 310. Although shown as positioned over a distal portion of wires 310, the membrane 370 can be positioned over other portions or the entire portion as discussed above with respect to the other membranes. The membrane 370 can also be attached to distal tubular portion 319 of the device 370, which is proximal of the soft atraumatic tip 321. As with the other membranes disclosed herein, a plurality of pores are preferably provided. The blocking device 300 (as well as blocking device 200 described above) can be connected to the thrombectomy wire 160 or 60 in the ways described above, or in alternative methods, which enable spinning of the thrombectomy wire without corresponding spinning of the blocking device 370.

In use of the thrombectomy apparatus (catheters) of the present invention, which by way of example is shown and described with respect to the embodiment of FIG. 2, it being understood the other thrombectomy device described herein can be inserted and used in a similar fashion, the thrombectomy apparatus 100 is inserted into the vessel through an access sheath (FIG. 16) in the femoral artery F and located via imaging. The device is advanced to the desired site and once in the select vessel, the flexible sheath 140 is retracted to first expose the blocking device, e.g. device 170, to allow expansion of the wires and membrane to the blocking position, followed by exposure of the thrombectomy wire, e.g. wire 160. Then, actuation button is depressed to actuate the motor, thereby causing wire 160 to rotate about its longitudinal axis, causing the arcuate regions 163,165 (FIG. 18) to directly contact and break up the thrombotic material inside the lumen of the graft or vessel. Note that the femoral location of the access sheath for introducing the thrombectomy apparatus 100 can be appreciated by the illustration in FIG. 16. Although the wires differ between apparatus 10 and apparatus 100, the introducer sheath location could be the same. The introducer sheaths can optionally have side ports for aspirating the small macerated particles. As shown in FIGS. 17 and 18, the device is advanced for example to the carotid artery.

FIGS. 11-13 illustrate an alternative embodiment of the thrombectomy apparatus of the present invention, designated generally by reference numeral 500. Thrombectomy apparatus 500 is similar to apparatus 10 of FIG. 1 except for the provision of two inflatable balloons and two lumens in the sheath (catheter), each communicating with one of the balloons to allow passage of inflation fluid. More specifically, apparatus 500 includes a flexible sheath (tube) 540 and a rotational wire 560 contained within sheath 540 identical in configuration and function to wire 60 of FIG. 1. A knob is rotatable to orient the J-tip and slide sheath 540 to uncover the rotational wire 560 in the same manner as knob 42 of FIG. 1. Note that FIG. 11 shows both balloons inflated for illustrative purposes since in the preferred use of the apparatus as discussed in detail below, only one balloon would be inflated at a time.

The flexible sheath 540 of apparatus 500 has a lumen 516, preferably circular in cross-section, for receiving the rotational wire 560, and first and second lumens 513, 514, each communicating with a balloon, for inflating the respectively balloon. More specifically, first lumen 513 communicates with angioplasty balloon 520, which is preferably somewhat elliptical shape, and second lumen 514 communicates with balloon 524, which is preferably substantially spherical in shape. Inlet ports communicate with lumens 513, 514, respectively, to inflate the respective balloons 520, 524.

In this embodiment which provides a double balloon thrombectomy apparatus, the apparatus reduces the procedural steps for thrombus removal. In the prior art, two independent balloon catheters plus a mechanical thrombectomy device are required to perform a thrombectomy procedure; with the apparatus 500, only one device is required. Thus, the numerous catheter insertions and removals can be avoided.

A clot blocking device such as any of those used with the previous embodiments is positioned at the distal end of the apparatus. For illustrative purposes, the blocking device 570 shown is identical to device 170 and the corresponding parts are labeled with designations "500". Therefore, blocking device 570 has wires 572 and membrane 580. Atraumatic tip 576 is attached to the distal end.

In the embodiment of FIG. 13A, the thrombectomy apparatus of FIG. 2 is provided with a balloon 624 identical to balloon 524 of FIG. 11. It can also, additionally or alternatively, include a balloon identical to balloon 520 of FIG. 11. Blocking device 670 is identical to blocking device 170 and includes wires 672 and membrane 680. Sinuous wire 660 extends from sheath 640. Atraumatic tip 676 is attached to the distal end.

In use of the double balloon thrombectomy device of FIG. 11, the venous access sheath is inserted, the thrombectomy device which contains an angioplasty balloon 520 is inserted through the sheath so tip 576 extends past the plaque. Angioplasty balloon 520 is inflated via lumen 513 to remove and compress the plaque P to open the lumen. Note the blocking device 570, positioned distal of balloon 520, is in the expanded configuration to block the flow of large plaque particles. The angioplasty balloon 520 is then deflated and the apparatus 500 is moved proximally so the rotational thrombectomy wire 560 is in the region of the blood clot. The apparatus is then activated to spin the wire 560 to break up the thrombus and other obstructive material. The wire can have a J-tip as in FIG. 1 or a sinuous configuration as in FIG. 2. Suction can then optionally be applied either with the apparatus in place, with the particles being removed through the gap between the flexible sheath 540 and the introducer sheath, or the apparatus can be removed and suction applied through the introducer sheath. Particles captured by the blocking device 570 can also be removed by suction. The blocking device 570 in the expanded configuration of FIG. 13 blocks the flow of large clots.

After breaking up the blood clot, if used in a dialysis graft clearing procedure, the apparatus is removed from venous access sheath and inserted through an arterial access sheath. The apparatus 500 is inserted so the tip extends slightly beyond the arterial anastomotic site, past the arterial plug (clot), and the spherical distal balloon 524 is inflated. The apparatus is then pulled proximally so that balloon 524 pulls the arterial plug into the graft G. The thrombectomy apparatus 500 can then be actuated to rotate wire 560 to break up the clot and other obstructive material, and optionally the broken particles can be removed by suction as described above. Particles captured by blocking device 570 can also be removed by suction. The thrombectomy apparatus 500 is then removed through the arterial access sheath, completing the thrombectomy procedure.

It is also contemplated that as an alternative to the double balloon thrombectomy devices described above, a single balloon thrombectomy device can be provided. This device could contain either angioplasty balloon 520 or balloon 524. If only balloon 520 is provided, although the procedure would still require a separate balloon catheter to remove the arterial plug, it would still advantageously eliminate the step and expense of a separate angioplasty catheter. Alternatively, if the single balloon device contained only balloon 524, although the procedure would require a separate angioplasty balloon catheter, it would still advantageously eliminate the step and expense of a separate balloon catheter for pulling the arterial plug into the graft.

It should also be appreciated that the double balloon concept to facilitate and expedite the surgical thrombectomy procedure can be utilized with other thrombectomy devices. For example, mechanical thrombectomy devices utilizing rotating wire baskets, fluid jet (hydrodynamic) devices applying high pressure fluid, devices utilizing brushes having bristles to scrape the clot and devices with rotating impellers can be modified to incorporate one or more balloons, i.e. an angioplasty and/or distal balloon to perform an angioplasty procedure and/or pull an arterial plug into the graft.

The blocking devices disclosed herein can be utilized with any of the wire embodiments disclosed herein as well as with other thrombectomy devices to block clots from traveling downstream.

FIG. 19 illustrates an alternate embodiment of a thrombectomy apparatus 700 having a blocking device 710. The thrombectomy device includes a rotatable basket 720 comprising a plurality of wires 722. The wires 722 expand to the expanded position shown when exposed from sheath 704. Rotation of basket 720 breaks up thrombus, and blocking device 710, composed of expandable wires 702 and membrane 704, similar to blocking device 70, blocks large particles from flowing downstream. The other blocking devices disclosed herein can also be used with the apparatus 700.

In the embodiment of FIG. 20, the wires 722' of basket 720' can include a shrink wrap material 724 thereover or a coating as shown to provide a less abrasive surface. The shrink wrap can include PET, Teflon, Pebax, polyurethane or other polymeric materials. This material helps to prevent the native vessel from being caught in the coil and reduce vessel spasms. Alternatively, instead of shrink wrap, a coating can be applied to the wires 722'. Coatings which can be utilized include for example hydrophilic coatings and PTFE. Blocking device 710' is identical to blocking device 710. Other blocking devices could also be utilized.

The various thrombectomy apparatus described herein can be utilized in a variety of applications, including but not limited to grafts, AV fistulas, deep vein thrombosis (e.g. in iliac or femoral vein), pulmonary embolism (e.g. in pulmonary artery) and neuro applications (e.g. in carotid or cerebral arteries).

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A thrombectomy apparatus for breaking up thrombus or other obstructive material in a lumen of a vascular graft or vessel, the apparatus comprising a thrombectomy wire having a first configuration and a second deployed configuration when exposed from a sheath, the wire having a straighter configuration in the first configuration, the wire being operatively connected to a motor for rotation of the wire to contact and break up the thrombus or other obstructive material, and a blocking device at a distal portion of the apparatus and connected to the thrombectomy wire such that the blocking device is advanced together with the thrombectomy wire into the lumen of the graft or vessel, the blocking device movable between a collapsed configuration and an expanded configuration, the blocking device in the expanded configuration configured to block thrombus dislodged by rotation of the wire.

2. The thrombectomy apparatus of claim 1, wherein the wire is sinuous in configuration and assumes its sinuous configuration when in the deployed configuration.

3. The thrombectomy apparatus of claim 1, wherein the wire is composed of an inner core and an outer coil.

4. The thrombectomy apparatus of claim 3, wherein the inner core is composed of a plurality of wires twisted together.

5. The thrombectomy apparatus of claim 1, wherein the wire spins independent of the blocking device such that the blocking device remains substantially stationary as the wire rotates.

6. The thrombectomy apparatus of claim 1, wherein the blocking device includes a tubular portion connected to a distal end of the wire, the wire rotatable independent of the tubular portion.

7. The thrombectomy apparatus of claim 6, further comprising an inflatable balloon, the balloon spaced proximally of a distal tip of the wire.

8. The thrombectomy apparatus of claim 1, wherein the wire terminates in a J-tip.

9. The thrombectomy apparatus of claim 1, further comprising a flexible sheath.

10. The thrombectomy apparatus of claim 9, further comprising first and second balloons, and the flexible sheath has first and second lumens, the first lumen communicating with the first balloon and the second lumen communicating with the second balloon.

11. The thrombectomy apparatus of claim 10, wherein the first balloon is an angioplasty balloon and the second balloon is configured for engaging and pulling an arterial plug, wherein the first balloon is proximal of the second balloon.

12. The thrombectomy apparatus of claim 1, further comprising a housing, the wire extending from the housing, the housing containing a battery and the motor for rotating the wire.

13. The thrombectomy apparatus of claim 1, wherein the blocking device includes a plurality of wires and a porous material covering at least a portion of the wires.

14. The thrombectomy apparatus of claim 13, wherein the material covers a distal portion of the wires.

15. The thrombectomy apparatus of claim 1, wherein the blocking device includes an expandable material and a plurality of wires expandable to expand the material.

16. The thrombectomy apparatus of claim 1, wherein in the second configuration the wire has a first arcuate region extending in a first direction and a second arcuate region spaced longitudinally from the first arcuate region and extending in a second direction, the first and second arcuate regions configured to break up thrombotic material as the wire spins.

17. A thrombectomy apparatus for breaking up thrombus comprising a rotatable thrombectomy wire, the wire having a non-linear configuration, a blocking device connected to a distal portion of the wire distally of the non-linear portion of the wire, the blocking device advanceable together with the thrombectomy wire and expanding radially with respect to the wire, and a motor for rotating the wire to break up thrombotic material as the wire rotates about its axis.

18. The apparatus of claim 17, wherein the wire is rotatable independent of the blocking device.

19. The apparatus of claim 18, wherein the wire includes a multifilar outer wire surrounding at least a portion of an inner core, the multifilar outer wire including at least first and second metal wires wound side by side and having a sinuous shaped portion at a distal region and a polymeric material surrounding at least a distal portion of the multifilar wire.

20. A method for breaking up thrombotic material from a lumen of a vascular graft or vessel comprising;

inserting a sheath;

inserting a thrombectomy apparatus having a rotatable thrombectomy wire and a blocking device connected to the thrombectomy wire;

exposing the rotatable thrombectomy wire of the thrombectomy apparatus from the sheath to enable the blocking device to move from a collapsed position to an expanded position;

rotating the wire to break up thrombotic material; and blocking at least some of the thrombotic material with the blocking device positioned at a distal portion of the thrombectomy wire; and withdrawing the thrombectomy wire to withdraw the blocking device.

21. The method of claim 20, wherein the step of rotating the wire includes the step of rotating the wire while the blocking device does not rotate.

22. The method of claim 21, wherein the blocking device is movable to the collapsed position for withdrawal.

\* \* \* \* \*